US008617863B2

(12) United States Patent
Koepf et al.

(10) Patent No.: US 8,617,863 B2
(45) Date of Patent: Dec. 31, 2013

(54) COMPOSITION, METHOD, AND KIT FOR PREPARING PLASMIN

(75) Inventors: Edward Koepf, Durham, NC (US); Thomas Zimmerman, Raleigh, NC (US)

(73) Assignee: Grifols Therapeutics Inc., Research Triangle Park, NC (US)

( * ) Notice: Subject to any disclaimer, the term of this patent is extended or adjusted under 35 U.S.C. 154(b) by 409 days.

(21) Appl. No.: 12/995,447

(22) PCT Filed: Jun. 3, 2009

(86) PCT No.: PCT/US2009/046152
§ 371 (c)(1),
(2), (4) Date: Mar. 18, 2011

(87) PCT Pub. No.: WO2009/149199
PCT Pub. Date: Dec. 10, 2009

(65) Prior Publication Data
US 2011/0201077 A1    Aug. 18, 2011

Related U.S. Application Data

(60) Provisional application No. 61/058,677, filed on Jun. 4, 2008.

(51) Int. Cl.
*C12N 11/10* (2006.01)
(52) U.S. Cl.
USPC .......................................... 435/174; 435/217
(58) Field of Classification Search
USPC .......................................... 435/174, 217, 192
See application file for complete search history.

(56) References Cited

U.S. PATENT DOCUMENTS

| | | | |
|---|---|---|---|
| 2,677,642 A | 5/1954 | Frank et al. |
| 2,677,643 A | 5/1954 | Frank et al. |
| 2,691,620 A | 10/1954 | Frank et al. |
| 2,701,227 A | 2/1955 | Frank et al. |
| 2,784,145 A | 3/1957 | Frank et al. |
| 3,136,703 A | 6/1964 | Singher |
| 3,226,304 A | 12/1965 | Siiteri et al. |
| 3,255,094 A | 6/1966 | Mather et al. |
| 3,419,472 A | 12/1968 | Siiteri et al. |
| 3,434,929 A | 3/1969 | Buck et al. |
| 3,444,045 A | 5/1969 | Derenzo et al. |
| 3,639,213 A | 2/1972 | Ginger et al. |
| 3,865,692 A | 2/1975 | Holleman et al. |
| 3,950,223 A | 4/1976 | Yugari et al. |
| 3,950,513 A | 4/1976 | Jensen |
| 3,980,772 A | 9/1976 | Ginger et al. |
| 4,082,612 A | 4/1978 | Robbins et al. |
| 4,115,551 A | 9/1978 | Lormeau et al. |
| 4,177,262 A | 12/1979 | Lormeau et al. |
| 4,259,448 A | 3/1981 | Nakamura et al. |
| 4,305,926 A | 12/1981 | Everse et al. |
| 4,361,652 A | 11/1982 | Uemura et al. |
| 4,361,653 A | 11/1982 | Watanabe et al. |
| 4,381,346 A | 4/1983 | Huasin et al. |
| 4,418,052 A | 11/1983 | Wong |
| 4,442,213 A | 4/1984 | Heber et al. |
| 4,446,316 A | 5/1984 | Chazov et al. |
| 4,462,980 A | 7/1984 | Diedrichsen et al. |
| 4,499,073 A | 2/1985 | Tenold |
| 4,551,271 A | 11/1985 | Hochuli et al. |
| RE32,271 E | 10/1986 | Husain et al. |
| 4,631,211 A | 12/1986 | Houghten |
| 4,652,639 A | 3/1987 | Stabinsky |
| 4,663,146 A | 5/1987 | Morser et al. |
| 4,774,087 A | 9/1988 | Wu et al. |
| 4,877,830 A | 10/1989 | Dobeli et al. |
| 4,908,204 A | 3/1990 | Robinson et al. |
| 5,024,829 A | 6/1991 | Berger et al. |
| 5,068,106 A | 11/1991 | Paques et al. |
| 5,096,637 A | 3/1992 | DiLeo et al. |
| 5,112,609 A | 5/1992 | Johnston et al. |
| 5,149,533 A | 9/1992 | Mulvihill et al. |
| 5,165,912 A | 11/1992 | Selmer et al. |
| 5,237,050 A | 8/1993 | Boyle et al. |
| 5,242,828 A | 9/1993 | Bergstrom et al. |
| 5,288,489 A | 2/1994 | Reich et al. |
| 5,290,692 A | 3/1994 | Suzuki et al. |
| 5,304,383 A | 4/1994 | Eibl et al. |
| 5,328,996 A | 7/1994 | Boyle |
| 5,334,384 A | 8/1994 | Mannix et al. |

(Continued)

FOREIGN PATENT DOCUMENTS

| | | |
|---|---|---|
| CA | 2045869 | 12/1991 |
| CN | 1 167 823 A | 12/1997 |

(Continued)

OTHER PUBLICATIONS

Reed et al., Identification of a Plasminogen Binding Region in Streptokinase That Is Necessary for the Creation of a Functional Streptokinase-Plasminogen Activator Complex. Biochemistry, 34: 10266-10271, 1995.*
Chica et al., Semi-rational approaches to engineering enzyme activity: combining the benefits of directed evolution and rational design. Current Opin. Biotechnol. 16(4):378-84, 2005.*
Sen et al., Developments in Directed Evolution for Improving Enzyme Functions. Appl. Biochem Biotechnol. 143(3):212-223, 2007.*
Caballero, A.R., et al., "Cloning, Expression, Sequence Analysis and Characterization of Streptokinases Secreted by Porcine and Equine isolates of *Streptococcus equisimilis*," *Infection and Immunity*, 67(12) :6478-6486 (1999).

(Continued)

*Primary Examiner* — Tekchand Saidha
*Assistant Examiner* — Rama P Ramanujam
(74) *Attorney, Agent, or Firm* — Womble Carlyle Sandridge & Rice, LLP

(57) ABSTRACT

A streptokinase immobilized on a surface, in particular an immobilized plasmin-resistant streptokinase, and compositions, methods and kits of utilizing same for preparing plasmin are provided.

20 Claims, 7 Drawing Sheets

(56) References Cited

U.S. PATENT DOCUMENTS

| | | | |
|---|---|---|---|
| 5,371,007 A | 12/1994 | Linnau et al. | |
| 5,407,673 A | 4/1995 | Reich et al. | |
| 5,407,678 A | 4/1995 | Rose et al. | |
| 5,472,692 A | 12/1995 | Liu et al. | |
| 5,587,291 A | 12/1996 | Binder et al. | |
| 5,629,213 A | 5/1997 | Kornguth et al. | |
| 5,728,674 A | 3/1998 | Sprecher et al. | |
| 5,767,269 A | 6/1998 | Hirsh et al. | |
| 5,776,452 A | 7/1998 | Eibl et al. | |
| 5,854,049 A | 12/1998 | Reed et al. | |
| 5,868,720 A | 2/1999 | Van Antwerp et al. | |
| 5,876,999 A | 3/1999 | Wu et al. | |
| 5,879,923 A | 3/1999 | Yaw et al. | |
| 5,928,218 A | 7/1999 | Gelbfish | |
| 6,139,819 A | 10/2000 | Unger et al. | |
| 6,183,692 B1 | 2/2001 | Trese et al. | |
| 6,207,066 B1 | 3/2001 | Trese et al. | |
| 6,218,517 B1 | 4/2001 | Suzuki | |
| 6,270,672 B1 | 8/2001 | Turecek et al. | |
| 6,309,873 B1 | 10/2001 | Torrens Madrazo et al. | |
| 6,312,893 B1 | 11/2001 | Van Ness et al. | |
| 6,355,243 B1 | 3/2002 | Novokhatny et al. | |
| 6,406,921 B1 | 6/2002 | Wagner et al. | |
| 6,413,759 B1 | 7/2002 | Madrazo et al. | |
| 6,444,422 B2 | 9/2002 | Van Ness et al. | |
| 6,479,253 B1 | 11/2002 | Silver et al. | |
| 6,538,103 B1 | 3/2003 | Ji et al. | |
| 6,613,508 B1 | 9/2003 | Van Ness et al. | |
| 6,623,928 B2 | 9/2003 | Van Ness et al. | |
| 6,664,112 B2 | 12/2003 | Mulligan et al. | |
| 6,694,764 B1 | 2/2004 | Eckstein, Jr. et al. | |
| 6,946,438 B1 | 9/2005 | Koike et al. | |
| 6,964,764 B2 | 11/2005 | Zimmerman et al. | |
| 6,969,515 B2 | 11/2005 | Jesmok et al. | |
| 7,105,327 B1 | 9/2006 | Kuppusamy et al. | |
| 7,253,264 B1 | 8/2007 | Lauffler et al. | |
| 7,547,435 B2 | 6/2009 | Pakola et al. | |
| 7,776,026 B2 | 8/2010 | Trese et al. | |
| 8,093,032 B2 * | 1/2012 | Kumar et al. | 435/216 |
| 2002/0192794 A1 | 12/2002 | Dadd et al. | |
| 2003/0012778 A1 | 1/2003 | Zimmerman | |
| 2005/0124036 A1 | 6/2005 | Susilo | |

FOREIGN PATENT DOCUMENTS

| | | |
|---|---|---|
| EP | 0 009 879 A1 | 4/1980 |
| EP | 0 256 836 A1 | 2/1988 |
| EP | 0 399 321 A2 | 11/1990 |
| EP | 0397 366 A1 | 11/1990 |
| GB | 904478 A | 8/1962 |
| GB | 985498 A | 3/1965 |
| GB | 2 090 599 A | 7/1982 |
| JP | 0207 8633 | 3/1990 |
| JP | 0906 5895 | 3/1997 |
| RO | 103 682 A | 12/1991 |
| WO | WO 87/06836 A | 11/1987 |
| WO | WO 93/15189 A | 8/1993 |
| WO | WO 94/23668 A1 | 10/1994 |
| WO | WO 95/04077 A1 | 2/1995 |
| WO | WO 95/20416 A1 | 8/1995 |
| WO | WO-96-38726 A1 | 12/1996 |
| WO | WO 97/15572 | 5/1997 |
| WO | WO 97/27331 A2 | 7/1997 |
| WO | WO 98/37086 A1 | 8/1998 |
| WO | WO 99/05322 A1 | 2/1999 |
| WO | WO 01/36611 | 2/2001 |
| WO | WO-01-81365 A2 | 11/2001 |
| WO | WO 01/94366 A1 | 12/2001 |
| WO | WO 02/50290 A1 | 6/2002 |
| WO | WO 03/054232 A2 | 7/2003 |
| WO | WO 2004/052228 A2 | 6/2004 |
| WO | WO 2005/105990 A2 | 11/2005 |
| WO | WO 2007/047874 A2 | 4/2007 |
| WO | WO 2009/073471 A1 | 6/2009 |

OTHER PUBLICATIONS

Cload, S.T., et al., "Development of Improved tRNAs for in vitro biosynthesis of proteins containing unnatural amino acids," *Chem. Biol.*, 3: 1033-1038 (1996).

De Renzo, E.C., et al., "Preparation and Certain Properties of Highly Purified Streptokinase," *J. Biol. Chem.* 242(3): 533-542 (1967).

Deutsch, D.G., et al., "Plasminogen: Purification from Human Plasma by Affinity Chromotography," *Science*, 170: 1095-1096 (1970).

Einarsson, M., et al., "Characterization of Highly Purified Native Streptokinase and Altered Streptokinase After Alkaline Treatment," *Biochim. Biophys. Acta* 568:19-29 (1979).

Ellman, J., et al., "Biosynthetic Method for Introducing Unnatural Amino Acids Site-Specifically into Proteins," *Methods Enzym.*, 202: 301-336 (1991).

Hagenson, M.J. et al., "Expression of Streptokinase in *Pichia pastoris* yeast," *Enzyme. Microb. Technol.* 11:650-656 (1989).

Kulisek, E.S., et al., "A Chromogenic Assay for the Detection of Plasmin Generated by Plasminogen Activator Immobilized on Nitrocellulose Using a *para*-Nitroanilide Synthetic Peptide Substrate," *Analytical Biochemistry 177*: 78-84 (1989).

Lizano, S., et al., "Streptokinase-Mediated Plasminogen Activation Using a Recombinant Dual Fusion Protein Construct. A Novel Approach to Study Bacterial-Host Protein Interactions," *J. Microbiot Methods*, 23: 261-280 (1995).

Malke, H., et al., "Expression of a Streptokinase Gene from *Streptoccis equisimilisin Streptococcus sanguis*," *Mot Gen. Genet.* 196: 360-363 (1984).

Malke, H., et al., "Nucleotide Sequence of the Streptokinase Gene from *Streptococcus equisimilis* H46A," *Gene 34*: 357-362 (1985).

Malke, H., et al., "Streptokinase: Cloning, Expression and Excretion by *Escherichia coli*," *Proc. Nat'l Acad. Sci.* 81:3557-3561 (1984).

Noren, C.J., et al., "A genral Method for Site-Specific Incorporation of Unnatural Amino Acids into Proteins," *Science*, 244: 182-188 (1989).

Rimon, A., et al., "Studies on the Activation of Plasminogen: Preparation and Properties of an Insoluble Derivative of Streptokinase," *Biochem. Biophy. Acta 73*: 301-310 (1963).

Shi, G-Y., et al., "Function of Streptokinase Fragments in Plasminogen Activation," *Biochem. J.* 304: 235-241 (1994).

Sugitachi, A., et al., "Immobulization of Plasminogen Activator, Urokinase, on Nylon," *Thrombos. Haemostas (Stuttg.)* 39: 426-436 (1978).

Wong, S-L., et al., "Engineering and Production of Streptokinase in a *Bacillus subtilis* Expression-Secretion System," *Applied and Env. Microbiol.* 60(2): 517-523 (1994).

Wu, X-C., et al., "Engineering of Plasmin-Resistant Forms of Streptokinase and their Production in *Bacillus subtilis*: Streptokinase with Longer Functional Half-Life," *Applied and Envir. Micro.*, 64(3):824-829 (1998).

Abe, et al., "Immobilized urokinase column as part of a specific detection system for plasminogen species separated by high-performance affinity chromatography," *J. Chromatography*, (1991), vol. 565, pp. 183-195.

Abe, T., "Fibrinolytic Influence of monocarbonic acids and some other substances," Proc. Intern. Cong. Hematol., (1962), vol. 3; pp. 1587-39.

Alkjaersig, N., et al, "The Activation of Human Plasminogen," *J. Biol. Chem.*, 233(1): 81-85 1958.

Alkjaersig, N., et al, "The Mechanism of Clot Dissolution by Plasmin," *J. Clin. Invest.*, 38(7): 1086-1095 1959.

Ambrus, C., et al., "Insolubilized Activators of the Fibrinolysin System," *J. Med.* 3:270-281 (1972).

Ambrus, J.L., et al., "Clinical Pharmacology of various types of fibrinolytic enzyme preparations," *Am. J. Cardiol.*, 6:462-475 (1960).

Amor, M. et al , "Thrombectomy with the hydrolysing catheter," Archives des Maladies du *Couer et des Vaisseaux*, (1997), vol. 90, No. 6,. 797-804.

Amris, C.J., et al, "Effect of Plasmin Therapy on Blood Coagulation and on Plasma Proteins in Patients with Cancer," *Danish Medical Bulletin*, 11(5):141-145 (1964).

(56) References Cited

OTHER PUBLICATIONS

Amris, C.J., et al., "Infusion of porcine plasmin in man," Scandivay. J. Clin. & Lab. Investigation, (1963), vol. 15, pp. 179-188.

Amris, C.J., et al., "Turnover and Distribution of [1]1-Labelled Procine Plasmin in Man and Dog," Danish Medical Bulletin, 11(5):146-152 (1964).

Amris, et al., "Clinical studies on an activator free porcine plasma (plasmin-novo)," SANGRE 9 (BARC), (1964), vol. 61, pp. 12-18.

Andrianov, S.I., et al., "Peculiarities of Hydrolytic Action of Plasmin, Miniplasmin, Microplasmin and Trypsin on Polymeric Fibrin," Ukr. Biokhim. Zh., 64(3): 14-20 (1992).

Anlyan, W., et al., "Experiences with Fibrinolysin in Peripheral Vascular Occlusive Disease," Am. J. Cordiol., 6:507-512 (1960).

Anonick, P., of al., "Regulation of Plasmin, Miniplasmin and Streptokinase—Plasmin Complex By—a-2-Antiplasmin, a-2-Macroglobulin, and Antithrombin III in the Presence of Heparin," Thrombosis Res., 59: 449-462 (1990).

Ambrus, et al., "Clinical and experimental studies on fibrinolytic enzymes," Ann NY Acad Sci., (Aug. 30, 1957), vol. 68, No. 1, p.s. 97-137.

Aronen, H.J, et al., "99mTc-plasmin test in deep vein thrombosis of the leg," Eur. J. Nuc. Med., 10:10-12 (1985).

Barrett, A.J., et al., "The Electrophoretically 'Slow' and 'Fast' Forms of the a2-Macroglobulin Molecule," Biochem. J., 181:401-418 (1979).

Barth, K.H. et al., "Multicenter prospective randomized comparison between a mechanical thrombectomy systems (OASIS) and pulespray thrombolysis for thrombosed hemodialysis grafts," Radiology, (Nov. 1998) vol. 209P, Supp. [S]: 714.

Beathard, G. A., "Mechanical versus pharmacomechanical thrombolysis for the treatment of thrombosed dialysis access grafts," Kidney International, (1994), vol. 45, pp. 1401-1406.

Becker, Gary J., Local Thrombolytic Therapy: Bridging the 'Generation Gap, Am. J. RoentgenoL, 140(2): 403-405 (1983).

Bennett, D., et al., "Kinetic Characterization of the Interaction of Biotinylated Human Interleukin 5 with an Fc Chimera of its Receptor a Subunit and Development of an ELISA Screening Assay using Real-Time Interaction Biosensor Analysis," I Molecular Recognition, 8: 52-58 (1995).

Bhisitkul, R.B., "Anticipation for enzymatic vitreolysis," Br. J. OphthalmoL, 85: 1-3 (2001).

Binder, B.R., et al., "Purification and Characterization of Human Vascular Plasminogen Activator Derived from Blood Vessel Perfusates," Journal of Biological Chemistry, 254(6):1998-2003 (1979).

Bookstein, J.J., et al., How I Do It: Pulse-spray pharmacomechanical thrombolysis, Cardiovasc. Intervent Radiol., (1992) vol. 15, pp. 228-233.

Boucek, R., et al., "Segmental Perfusion of the Coronary Arteries with Fibrinolysin in Man Following a Myocardial Infarction," Am. J. Cardiol., 6:525-533 (1960).

Bowie, J.U., et al., "Deciphering the Message in Protein Sequences: Tolerance to Amino Acid Substitutions," Science, 247: 1306-1310 (1990).

Boyles, P.W., et al., "Comparative effectiveness of intravenous and intra-arterial fibrinolysis therapy," Am. J. Cardio!., 6:439-446 (1960).

Browse, N., "Deep Vein Thrombosis," British Medical Journal, 4:676-678 (1969).

Burck, P.J., et al., "Characterization of a Modified Human Tissue Plasminogen Activator Comprising a Kringle-2 and a Protease Domain, " J Biol. Chem., 265(9): 5170-5177 (1990).

Burgin, J. and J. Shaller, "Expression, Isolation and Characterization of a Mutated Human Plasminogen Kringle 3 with a Functional Lysine Binding Site," Cell. Mal. Life. Sci. 55: 135-141 (1999).

Cao, Y., et al., "Kringle Domains of Human Angiostatin," J. Biol. Chem., 271(46): 29461-29467 (1996).

Castellino, F.J. and J.R. Powell, "Human Plasminogen," Meth. Enzymology 80:365-378 (1981).

Castellino, F.J., and S.G. McCance, "The kringle domains of human plasminogen," Ciba Found. Symp., 212: 46-65 (1997).

Castellino, F.J., et al., "Rabbit Plasminogen and Plasmin Isozymes," Methods in Enzymology, 45:273-286 (1976).

Chang, Y., et al., "Structure and Ligand Binding Determinants of the Recombinant Kringle 5 Domain of Human Plasminogen," Biochemistry, 37: 3258-3271 (1998).

Chase, T. and E. Shaw, "Titration of Trypsin, Plasmin, and Thrombin with p-Nitrophenyl 0-Guanidinobenzoate HCI," Methods EnzymoL, 19: 20-27 (1970).

Christensen et al., Stopped-flow fluorescence kinetics of bovine α2-antiplasmin inhibition of bovine midiplasmin, Biochem. J. 305:97-102 (1995).

Collen D., et al., "On the Regulation and Control of Fibrinolysis," Throm. Haemost., 43: 77-89 (1980).

Collen D., et al., "Thrombolysis with human extrinsic (tissue-type) plasminogen activator in rabbits with experimental jugular vein thrombosis. Effect of molecular form and dose of activator, age of the thrombus, and route of administration," J. of Clin. Invest., 71(2):368-376 (1983).

Cunningham, B.C., and J.A. Wells, "High-Resolution Epitope Mapping of hGH-Receptor Interactions by Alanine-Scanning Mutagenesis," Science, 244: 1081-1085 (1989).

Dahl, 0.E., et al., "99mTc-Plasmin Uptake Test is Unreliable for Diagnosing Asymptomatic Deep Vein Thrombosis After Hip Replacement Surgery," Thrombosis Research, 62:781-784 (1991).

de Vos, A.M., et al., "Human Growth Hormone and Extracellular Domain of Its Receptor: Crystal Structure of the Complex," Science, 255: 306-312 (1992).

Deacon, et al., "Technetium 99m-plasmin: a new test for the detection of deep vein thrombosis," Eur J. Nucl. Med., (1980), vol. 53, No. 631, pp. 673-677.

Decision of the Board of Patent Appeals and Interferences dated Feb. 19, 2008 in Appeal No. 2007-0545, Ex parte Thomas P. Zimmerman, Valery Novokhatny, Shang Jiang and James' Colancleve (with claims considered on Appeal).

Douglas, J.T., et al., "The Two-Domain NK1 Fragment of Plasminogen: Flding, Ligand Binding, and Thermal Stability Profile," Biochemistry, 41(10): 3302-3310 (2002).

Dupe, F et al., "Acyl-enzymes as thrombolytic agents in dog models of venous thrombosis and pulmonary embolism," Thrombosis and Haemostasis, (1981), vol. 51, No. 2, pp. 248-253.

Edenbrandt, C.M., et al., "Comparison between 99Tcm-porcine plasmin and 99Tcm-labelled erythrocytes in diagnosis of deep vein thrombosis," Clinical Physiology 4:243-252 (1984).

Edenbrandt, C.M., et al., "Diagnosis of Deep Venous Thrombosis by 99mTc-Human Serum Albumin Microcolloid," Eur J Nucl Med 8:332-334 (1983).

Edenbrandt, C.M., et al., "Follow-up of circulatory changes secondary to deep venous thrombosis with special regards to radionuclide tests," Clinical Physiology 6:153-161 (1986).

Edenbrandt, C.M., et al., "Return to normal of 99mTc-plasmin test after deep venous thrombosis and its relationship to vessel wall fibrinolysis," Eur J Nucl Med 12:197-200 (1986).

European Supplementary Partial Search Report (EP 00 97 8572, dated Jul. 16, 2004).

European Supplementary Partial Search Report (EP 00 99 0910, dated May 25, 2004).

European Supplementary Partial Search Report (EP 00 99 1956, dated Jun. 1, 2004).

Extended European Search Report (EP 1 956 082 Al, dated Jul. 10, 2008).

Freitag, H., et al., "Lys-plasminogen as an Adjunct to Local Intraarterial Fibrinolysis of Carotid Territory Stroke: Laboratory and Clinical Findings," Neuroradiology, 38:181-185 (1996).

Gandorfer, A., et al., "Posterior Vitreous Detachment Induced by Microplasmin," OVS, 45(2): 641-647 (2004).

Gandorfer, A., et al., "Ultrastructure of the viteoretinal interface following plasmin assisted vitrectomy," Br. J. Ophthalmol., 85: 6-10 (2001).

GE Healthcare—Affinity chromatography (Data File 18-1139-38 AC—first published Sep. 2000).

(56) References Cited

OTHER PUBLICATIONS

Goretzki, L., et al., "Binding of the NG2 Proteoglycan to Kringle Domains Modulates the Functional Properties of Angiostatin and Plasmin(ogen)," *J. Biol. Chem.*, 275(37): 2862528633 (2000).
Greig, at al., "Protamine-Heparin complex as a substrate for plasmin," *Biochim. Biophys, Ada.*, (1963), vol. 67, pp. 658-668.
Gribskov, M., and Richard R. Burgess, "Sigma factors from *E. coli, B. subtilis*, phage SP01, and phage T4 are homologous proteins," *Nucl. Acids Res.*, 14(6): 6745-6763 (1986).
Haidacher, D., et al., "Temperature effects in hydrophobic interaction chromatography," *Proc Natl Acad Sci USA* 93:2290-2295 (1996).
Hedner, U., et al., "Effects of Porcine Plasmin on the Coagulation and Fibdnolytic Systems in Humans," *Blood*, 51(1):157-164 (1978).
Holmberg, L., et al., "Purification of Urokinase by Affinity Chromatography," *Biochim. Biophys. Acta.*, 215-222 (1976).
Hoover, G.J., et al., "Amino Acids of the Recombinant Kringle 1 Domain of Human Plasminogen that Stabilize Its Interaction with 0)-Amino Acids," *Biochemistry*, 32(41): 10936-10943 (1993).
Horrevoets, A.J.G., at al., "Production and Characterization of Recominant Human Plasminogen (S741 C-Fluorescein): A Novel Approach to Study Zymogen Activation Without Generation of Active Protease," *J. Bio. Chem.*, 272(4): 2176-2182 (1997).
Horrevoets, A.J.G., et al., "The Activation-resistant Comformation of Recombinant Human Plasminogen Is Stabilized by Basic Residues in the Amino-terminal Hinge Region," *J. Bio. Chem.*, 270(26): 15770-15776 (1995).
Houghten, R.A., "General method for the rapid solid-phase synthesis of large numbers of peptides: Specificity of antigen-antibody interaction at the level of individual amino acids," *Proc. Natl. Acad. Sci. USA*, 82: 5131-5135 (1985).
Pharmacia Biotech., Data File: 18-1117-58 (AA Edition), Sephadex• ion exchange media; Ion exchange chromatography. Downloaded from world wide web on Dec. 11, 2010 (http://www.chembio.uoguelph.ca/educmat/chm357/sephadex.pdf).
Martin, L., "Acid-Base Balance," in Pulmonary Physiology in Clinical Practice, The Essentials for Patient Care and Evaluation, Chapter 7, pp. 1-4. Downloaded from world wide web on Nov. 29, 2011 (http://lakesidepress.com/pulmonary/books/physiology/chap7_1.htm).
Hunt and Novokhatny, Journal of Thrombosis and Haemostasis 2005; 3(1): Abstract No. P0781, for $20^{th}$ International Society on Thrombosis and Haemostasis Congress, Sydney, Australia.
Hunt and Novokhatny, Poster presented Tuesday, Aug. 9, 2005 at $20^{th}$ International Society on Thrombosis and Haemostasis Congress, Sydney, Australia.
Hunt, J.A., et al., "Simplified Recombinant Plasmin: Production and Functional Comparison of a Novel Thrombolytic Molecule with Plasma-Derived Plasmin," *Thromb, Haemost.*, 100: 413419 (2008).
International Search Report (PCT/US03/34020, dated Jul. 27, 2004).
International Search Report (PCT/US05/013562, dated Nov. 3, 2005).
International Search Report (PCT/US06/040940, dated Oct. 18, 2006).
Ito, et al., "Separation of Human Glu-Plasminogen, Lys-Plasminogen and Plasmin by High-Performance Affinity Chromatography on Asahipak GS Gel Coupled with pAminobebnzamidine," *Journal of Chromatography*, 348: 199-204 (1985).
IX. Plasmin In "Pharmaceutical Enzymes" (eds. R. Ruyssen & A. Lauwers)-Story Scientia, Gent, Belgium, (1978), pos. 123-131.
Jespersen, J., et al., The autodigestion of human plasmin follows a bimolecular mode of reaction subject to product inhibition, *Thromb. Res.* 41(3):395-404 (1986).
Johanson, K., et al., "Binding Interactions of Human Interleukin 5 with Its Receptor a Subunit," *J. Biol. Chem.*, 270(16): 9459-9471 (1995).
Johnson, A.J., et al., "Assay methods and standard preparations for plasmin, plasminogen and urokinase in purified systems, 1967-1968," *Thrornb. Diath. Haemorrh.*, 21(2):259-72 (1969).
Kirkwood, T.B.L., at al., "A standard for human plasmin," *Thromb. Diath. Haemorrh.*, 34(1):20-30 (1975).

Kitamoto, Y., et al., "A Femoral Vein Catheter with Immobilized Urokinase (UKFC) as an Antithrombotic Blood Access," *Trans. Am. Soc. Artif. Intern. Organs*, 33:136-139 (1987).
Kline, D.L. and J.B. Fishman, Preparation, Stabilization and Some Properties of Purified Human Plasmin, *Thromb. Diath. Haemorrh.*, 11:75-84 (1964).
Kline, D.L., "The Purification and Crystallization of Plasminogen (Profibrinolysin)," *Journal of Biological Chemistry* 204:949-955 (1953).
Knight, L.C., "Radiopharmaceuticals for Thrombus Detection," *Seminars in Nuclear Medicine*, 20(1):52-67 (1990).
Kolev, K., et al., "Functional Evaluation of the Structural Features of Proteases and Their Substrate in Fibrin Surface De radation," *J. Biol. Chem.*, 272(21): 13666-75 (1997).
Komorowicz, E., et al., "Fibrinolysis with Des-Kringle Derivatives of Plasmin and Its Modulation by Plasma Protease Inhibitors," *Biochemistry*, 37(25): 9112-9118 (1998).
Lagerstedt, C., et al., "99mTc plasmin in 394 consecutive patients with suspected deep venous thrombosis," *Eur J Nucl Med*, 15:771-775 (1989).
Langer-Safer et al., Replacement of finger and growth factor domains of tissue plasminogen activator with plasminogen kringle 1, *J. Biol. Chem.* 265(6):3715-3723 (25 Feb 199).
Larsen, V., "Fibrinolytic Enzyme in the Treatment of Patients with Cancer," *Danish Medical Bulletin*, 2(5):137-140 (1964).
Larson, V., at al., "Fibrinolytic Treatment with Activator-Free Porcine Plasmin," *Scand. J. Clin. Invest 18(Suppl. 89)*:34-73 (1966).
Lazzaro, C.R. et al., "Modified use of the arrow-trerotola percutaneous thrombolytic device for the treatment of trombosed hemodialysis access grafts," *J. Vasc Inter Radiol*, (Sep. 1999), vol. 10, No. 8, pp. 1025-1031.
Lee, H., et al., "Disruption of Interkringle Disulfide Bond of Plasminogen Kringle 1-3 Changes the Lysine Binding Capability of Kringle 2, But Not Its Antiangiogenic Activity," *Arch. Biochem. Biophys.*, 375(2): 359-363 (2000).
Lerch, P.G., et al., "Localization of Individual Lysine-Binding Regions in Human Plasminogen and Investigations on Their Complex-Forming Properties," *Eur. I Biochem.*, 107(1): 7-13 (1980).
Li, X., et al., "Posterior Vitreous Detachment with Plasmin in the isolated Human Eye," *Graefe's Arch. Clin. Exp. Ophthalmol.*, 240:56-62 (2002).
Lijnen, H.R., et al., "Activation of plasminogen by pro-urokinase," *J. Biol. Chem.*, 261(1):1253-1258 (1986).
Lin, L-F., et al., "Epsilon Amino Caproic Acid Inhibits Streptokinase—Plasminogen Activator Complex Formation and Substrate Binding through Kringle-Dependent Mechanisms," *Biochemistry*, 39: 4740-4745 (2000).
Ling, C.M., et al., "Mechanism of formation of bovine plasminogen activator from human plasmin," *J. Biol. Chem.*, 240(11):4213-8 (1965).
Lippschutz, E.L., et al., "Controlled study of the treatment of coronary occulsion with urokinase-activated human plasmin," *Am. J. Cardiot*, 16:93-98 (1965).
Lucas, M.A., et al., "The Binding of Human Plasminogen to Fibrin and Fibrinogen," *J. Biol. Chem.*, 258(7): 4249-4256 (1983).
Madison, E.L., "Probing Structure-Function Relationships of Tissue-Type Plasminogen Activator by Site-Specific Mutagenesis," *Fibrinolysis* 8 Supp.1:221-236 (1994).
Marder, V.J., et al., "Haemostatic Safety of a Unique Recombinant Plasmin Molecule Lacking Kringles 2-5," *Thromb. Haemost.*, 104: 780-787 (2010).
Marder, V.J., et al., "Plasmin Induces Local Thrombolysis without Causing Hemorrhage: A Comparison with Tissue Plasminogen Activator in the Rabbit," *Thromb Haemost*, 86:739-745 (2001).
Martin, at al., "Pulmonary Physiology in Clinical Practice, The. Essentials for Patient Care and Evaluation," The C.V. Mosby Company, 1987, Chap. 7, Acid-base balance,.129-146.
Mathey D.G., et al., "Intravenous Urokinase in Acute Myocardial Infarction," *Am. J. Cardiol.*, 55:878-882 (1985).
Matsuka, Y.V., et al., "Fluorescence spectroscopic analysis of ligand binding to kringle 1+2+3 and kringle 1 fragments from human plasminogen," *Eur. J. Biochem.*, 190: 93-97 (1990).

(56) References Cited

OTHER PUBLICATIONS

McCance, S., et al., "Amino Acid Residues of the Kringle-4 and Kringle-5 Domains of Human Plasminogen that Stabilize their Interactions with 0-Amino Acid Ligands," *J. Biol. Chem.*, 269(51): 32405-32410 (1994).

Medynski, D., et al., "Refolding, purification, and activation of miniplasminogen and microplasminogen isolated from *E. coli* inclusion bodies," *Protein Expression and Purification* 52:395-402 (2007).

Menhart, N., et al., "Functional Independence of the Kringle 4 and Kringle 5 Regions of Human Plasminogen," *Biochemistry*, 32: 8799-8806 (1993).

Milne, R.M., et al., "Postoperative Deep Venous Thrombosis: A Comparison of Diagnostic Techniques," *Lancet*, 2 (7722):445-447 (1971).

Mizutani et al. "Potential thrombolysis under selective infusion of autolotous plasmin (AP) solution," *Japanese Heart Journal*, 30(5):723-732 (1989).

Moser, K., "Effects of Intravenous Administration of Fibrinolysin (Plasmin) in MaR" *Circulation*, 20:42-55 (1959).

Motta, A., et al., "Complete Assignment of the Aromatic Proton Magnetic Resonance Spectrum of the Kringle 1 Domain from Human Plasminogen: Structure of the Ligand-Binding Site," *Biochemistry*, 26(13): 3827-3836 (1987).

Mukhopadhyay, A., "Inclusion Bodies and Purification of Proteins in Biologically Active Forms," *Advances in Bio. Eng./Biotech.* 56:61-109 (1997).

Nahum, L.H., et al., "Fibrinolysis. II. Evaluation of enzymatic thrombolysis: Experiments with plasmin preparations in arterial, venous thrombosis," *Conn. Med.* 24:139-46 (1960).

Nilsson, T. and B. Wiman, On the structure of the stable complex between plasmin and alpha- 2-antiplasmin, *FEBS Lett.*, 142(1):111-114 (1982).

Novokhatny, V. et al. "Thrombolytic potential of locally delivered active plasmin (Pm): In vitro assessment and in vivo comparison with tPA in the rabbit jugular vein thrombosis model," *Blood*, 92(10) Suppl. 2, Abstract 3400. (Nov. 15, 1998).

Novokhatny, V., and Stanislav A. Kudinov, "Domains in Human Plasminogen," *J. MoL Biol.*, 179: 215-232 (1984).

Novokhatny, V., at al., "Analysis of Ligand Binding to Kringles 4 and 5 Fragments from Human Plasminogen," *Thromb Res.*, 53(3): 243-52 (1989).

Novokhatny, V., et al., "Thrombolytic potency of acid-stabilized plasmin: superiority over tissue-type plasminogen activator in an in vitro model of catheter-assisted thrombolysis," *J Thromb. Haemost.*, 1(5): 1034-1041 (2003).

Novokhatny, V., et al., "Domain Structure and Domain-Domain Interaction of recombinant Tissue Plasminogen Activator," *J. Biol. Chem.* 266(20):12994-13002 (1991).

Obukowicz, M.G., et al., "Secretion of Active Kringle-2-Serine Protease in *Escherichia coli*," *Biochemistry* 29:9737-9745 (1990).

Ouellette, "Introduction to General, Organic, and Biological Chemistry," Second Edition (1988). The Ohio State University. Macmillan Publishing Company, New York, NY, 288-290.

Owunwanne, et al., "Technetium Tc 99m plasmin in the diagnosis of inflammatory disease," *Eur J. Nucl. Med.*, (1987), vol. 12, No. 10, pp. 496-499.

Patthy, L., et al., "Evolution of the Proteases of Blood Coagulation and Fibrinolysis by Assembly from Modules," *Cell* 41:657-663 (1985).

Perrson, B. and Darte, L., "Labeling Plasmin with Technetium-99m for Scintigraphic Localization of Thrombi," *International Journal of Applied Radiation and Isotopes*, 28:97-104 (1977).

Petitpretz, P., et al., "Effects of a single bolus of urokinase in patients with life-threatening pulmonary emboli: a descriptive trial," *Circulation*, 70(5): 861-866 (1984).

Powell, J.R., and Francis J. Castellino, "Activation of Human Neo-Plasminogen-Va1442 by Urokinase and Streptokinase and a Kinetic Characterization of Neo-Plasmin-Va1442," *J. Biol. Chem.*, 255(11): 5329-5335 (1990).

Quigley, J.P., "Plasminogen, the Serum Proenzyme Activated by Factors from Cells Transformed by Oncogenic Viruses," *J. Bio. Chem.* 249(13): 4300-4311 (1974).

Rasmussen, A., et al., "Distinction by Radioisotope Technique of a Subgroup with Increased Thrombophilic Potential among Patients Submitted to Major Abdominal Surgery," *Journal of Medicine*, 17(5-6):357-364 (1986).

Rejante, M.R. and M. Llinas, "Solution structure of the e-aminohexanoic acid complex of human plasminogen kringle 1," *Eur. J. Biochem.*, 221(3): 939-949 (1994).

Robbins, K.C. and L Summaria, "Plasminogen and Plasmin," *Meth. Enzymol.* 45:257-273 (1976).

Robbins, K.C. et al. "Purification of Human Plasminogen and Plasmin by Gel Filtration of Sephadex and Chromatography on Diethylaminoethyl Sephadex". *Journal of Biological Chemistry* (1963), vol. 238, pp. 952-962.

Robbins, K.C., et al., "The peptide chains of human plasmin. Mechanism of activation of human plasminogen to plasmin," *J. BioL Chem.*, 242(10):2333-42 (1967).

Robbins, KC., et al., "Human Plasminogen and Plasmin," *Methods in Enzymology*, 19:184-199 (1970).

S. Husain, "A single-step separation of the one-and two-chain forms of tissue plasminogen activator," *Arch Biochem Biophys.*, (1991), vol. 285, p.s. 373-376.

Sakata, Y., et al., "Differential binding of plasminogen to crosslinked and noncrosslinked fibrins: its significance in hemostatic defect in factorXIII deficiency," *Blood*, 63:1393-1401 (1984).

Schmer. "The purification of bovine thrombin by affinity chromatography on benzamidineagarose," *Hoppe Seyler's Z Physiol Chem.*, 353: 810-814 (1972).

Schwartz, R.M. and M.O. Dayhoff, "Matrices for Detecting Distant Relationships," *Atlas of Protein Sequence and Structure*, 5(3): 353-358 (1978).

Segel, "How to solve mathematical problems in general biochemsitry," *Biochemical Calculations*, $2^{nd}$ *Edition* (1976), pis. 83-85.

Seifert, V., et a/., "Efficacy of Single Intracisternal Bolus Injection of Recombinant Tissue Plasminogen Activator to Prevent Delayed Cerebral Vasospasrn after Experimental Subarachnoid Hemorrhage," *Neurosurgery*, 25(4): 590-598 (1989).

Semba et al., "Iliofemoral deep venous thrombosis: Aggressive therapy with catheter-directed thrombolysis," *Radiology*, (1994), vol. 191, pis. 487-494.

Sgouris, J,T, et al. "The preparation of human fibrinolysin (plasmin)," *Vox Sang.*, 5:357-76 (1960).

Sherry S., "The Origin of Thrombolytic Therapy," *J. Am. Coll. Cordiol.*, 14(4):1085-1092 (1989).

Shi, et al., "Differential autolysis of human plasmin at various pH levels," *Thrombosis Research*, 1988, vol. 51, pp. 355-364.

Shi, G-Y., et al., "Kringle Domains and Plasmin Denaturation," *Biochem. Biophys. Res. Comm.*, 178(1): 360-368 (1991).

Shimura, et al., "High-performance affinity chromatography of plasmin and plasminogen on a hydrophilic vinyl-polymer gel coupled with p-aminobenzamicline," *J. Chromatography*, (1984), vol. 292, pp. 369-382.

Smith, L.J., et al., "Human Interleukin 4: The Solution Structure of a Four-helix Bundle Protein," *J. MoL Biol.*, 224: 899-904 (1992).

Smith, T.F., and Michael S. Waterman, "Comparison of Biosequences," *Advances in Applied Mathematics*, 2: 482-489 (1981).

Söhndel, S., et al., "Recombinant Gene Expression and 1H NMR characteristics of the Kringle (2+3) Supermodule: Spectroscopic/Functional Individuality of Plasminogen Kringle Domains," *Biochemistry* 35:2357-2364 (1996).

Sottrup-Jensen, L., et al., "The Primary Structure of Human Plasminogen: Isolation of Two Lysine- Binding Fragments and One "Mini- " Plasminogen (MW, 38,000) by Elastase-Catalyzed-Specific Limited Proteolysis," *Prog. Chem. Fibrinol. Thrombol.*, 3: 191-209 (1978).

Stewart, D., et al., "Distinct dose-dependent effects of plasmin and TPA on coagulation and hemorrhage," *Blood*, 101(8): 3002-3007 (2003).

(56) References Cited

OTHER PUBLICATIONS

Suenson, E. and Thorsen, S., "Secondary-site binding of Glu-plasmin, Lys-plasmin and miniplasmin to fibrin," *Biochem. J.,* 197:619-628 (1981).
Summaria, L., et al., The specific mechanism of activation of human plasminogen to plasmin, *J. Biol. Chem.,* 242(19):4279-83 (1967).
Summaria, L., et al., "Recombinant human Lys-plasmin and the Lys-plasmin streptokinase complex," *J. Biol. Chem,* 254(14):6811-4 (1979).
Supplementary Partial European Search Report (EP 00 99 1956, dated Dec. 17, 2004).
Tengborn, L, et al., "Demonstration of 99m-Tc-Labelled Plasmin an the Surface of Ex Vivo Thrombi," *Thrombosis Research,* 28:783-791 (1982).
Thewes, T., of al., "Ligand Interactions with the Kringle 5 Domain of Plasminogen," *J. Biol. Chem.,* 265(7): 3906-3915 (1990).
Trese, M.T., "Enzymatic Vitreous Surgery," *Seminars in Ophthalmology,* 15(2): 116-121 (2000).
Ueshima, S., et al., "Stabilization of plasmin by lysine derivatives," *Clin. Chim. Acta.,* 245(1):7-18 (1996).
Uflacker R, et al., "Treatment of thrombosed dialysis access grafts: Randomized trial of surgical thrombectomy versus mechanical thrombectomy with the amplatz device," *JVIR,* (1996), vol. 7, No. 2, pp. 185-192.
Vali, Z. and Patthy, L, "The Fibrin-binding Site of Human Plasminogen," *Journal of Biological Chemistry,* 269 (22)13690-13694 (1984).
Van Zonneveld, A-J., et al., "Autonomous functions of structural domains on human tissue-type plasminogen activator," *PNAS,* 83: 4670-4674 (1986).
Verstraete, M., The Fibrinolytic System: from Petri Dishes to Genetic Engineering, *Thrombosis and Haemostasis,* 74(1):25-35 (1995).
Verstraeten, T.C., et al., "Pharmacologic Induction of Posterior Vitreous Detachment in the Rabbit," *Arch Ophthalmol.,,* 111: 849-854 1993.
Walker, B., et al., "Strategies for the inhibition of serine proteases," *CMLS. Cell. Mol. Life Sci.,* vol. 58, (2001), pp. 596-624.
Wang, F., et al., "Safety and Efficacy of Displase and Plasmin in Pharmacologic Vitreolysis," *OVS,* 45(9): 3286-3290 (2004).
Wang, J., et al., "Structure and Function of Microplasminogen: I. Methionine Shuffling, Chemical Proteolysis, and Proenzyme Activation," *Protein Sci.* 4:1758-1767 (1995).
Wang, S., et al., "Deletion of Ile 1 Changes the Mechanism of Streptokinase: Evidence for the Molecular Sexuality Hypothesis," *Biochemistry,* 38: 5232-5240 (1999).
Wang, Z-L, et al., "PVD Following Plasmin But Not Hyaluronidase: Implications for Combination Pharmacologic Vitreolysis Therapy," *Retina,* 25: 38-43 (2005).
Whisenant, B. K., et al., "Rheolytic thrombectomy with the Possis AngioJet: Technical considerations and Initial clinical experience," *J. of Invasive Cardiology,.* 11(7): 421-426 (1999).
Williams, J.G., et al., "Autologous Plasmin Enzyme in the Surgical Management of Diabetic Retinopathy," *Ophthalmology* 108(10): 1902-1905 (2001).
Wiman, B and Desire Collen, "Molecular Mechanism of Physiological Fibrinolysis," *Nature,* 272: 549-550 (1978).
Wiman, B. and Desire Collen, "On the Kinetics of the Reaction between Human Antiplasmin and Plasmin," *Eur. J. Biochem.,* 84: 573-578 (1978).
Wiman, B., "Affinity-chromatographic purification of human alpha 2-antiplasmin," *Biochem. J.,* 191M:229-232 (1980).
Wiman, B., et al., "On the Specific Interaction Between the Lysine-Binding Sites in Plasmin and Complementary Sites in a2—Antiplasmin and in Fibrinogen," *Biochim. Biophys. Acta,* 579: 142-154 (1979).
Wiman, B., and Per Wallén, "Activation of Human Plasminogen by an Insoluble Derivative of Urokinase Structural Changes of Plasminogen in the course of Activation to Plasmin and Demonstration of a Possible Intermediate Compound," *Eur. J. Biochem.,* 36(1): 25-31 (1973).
Wohl, R.C., et al., "Kinetics of Activation of Human Plasminogen by Different Activator Species at pH 7.4 and 37° C.," *J. Biol. Chem.,* 255(5): 2005-2013 (1980).
Wohl, R.C., et al., "Steady State Kinetics of Activation of Human and Bovine Plasminogens by Streptokinase and Its Equimolar Complexes with Various Activated Forms of Human Plasminogen," *J. Biol. Chem.,* 253(5): 1402-1407 (1978).
Wu, S-C., et al., A Fast-Acting Modular-Structured Staphylokinase Fusion with Kringle-1 From Human Plasminogen as the Fibrin-Targeting Domain Offers Improved Clot Lysis Efficacy, *J. Biol. Chem.* 278(20):18199-181206 (2003).
Wu, T P. et al., "The structure of recombinant plasminogen kringle 1 and the fibrin binding site," *Blood Coagul. Fibrinolysis,* 5(2): 157-166 (1994).
Zajicek, J., et al., "The Effects of Ligand Binding on the Backbone Dynamics of the Kringle 1 Domain of Human Plasminogen," *J. MoL Biol.,* 301(2): 333-347 (2000).
Zeit, R M., "Arterial and venous embolization: Declotting of dialysis shunts by direct injection of streptokinase," *Radiology,* (1986), vol. 159, No. 3, pp. 639-641.
CN 1167823A (Huang, C.) Dec. 17, 1997 (abstract) [online] Retrieved from Thomson Innovation, p. 1.
JP 0207 8633 (Green Cross Corp.) Mar. 19, 1990 (abstract) [online] Retrieved from Thomson Innovation, pp. 1-2.
JP 0906 5895 (Nitto Boseki Co. Ltd.) Mar. 11, 1997 (abstract) [online] Retrieved from Thomson Innovation, pp. 1-2.
RO 103 682 (Cantacuzino Inst.) Dec. 9, 1991 (abstract) [online] Retrieved from Espacenet, p. 1.
Wu, X.C., et al., "Engineering of Plasmin-Resistant Forms of Streptokinase and their Production in *Bacillus subtilis*: Streptokinase with Longer Functional half-Life," *Appl. Environ. Microbio.,* 64(3): 824-829 (1998).
Banjeree, A., et al., "Streptokinase—a Clinically Useful Thrombolytic Agent," *Biotech. Advances,* 22(4): 287-307 (2004).
Extended European Search Report (EP 9759358, dated Nov. 8, 2011).

\* cited by examiner (SEQ ID NO:3)
ggatcccATCGCTGGTCCCGAATGGCTCTTAGACCGTCCATCTGTGAATAACTCCCAACTTGTAGTATC
CGTTGCAGGCACCGTCGAAGGAACCAACCAAGACATCTCCTTAAAATTTTTTGAAATCGATTTAAC
CTCTCGTCCTGCCCATGGCGGAAAAACCGAACAAGGCCTCTCACCAAACTCTAAACCTTTTGCCAC
CGATTCAGGAGCTATGCCACACAAACTCGAAAAAGCCGACCTCTTAAAAGCTATCCAAGAACAAC
TTATCGCTAATGTACATTCAAATGATGATTATTTTGAAGTAATTGATTTTGCGTCTGATGCCACAAT
TACCGATCGCAATGGCAAAGTCTATTTTGCTGATAAAGACGGTAGCGTTACCTTGCCCACTCAGCC
AGTACAGGAATTCTTATTATCCGGCCACGTGCGCGTACGTCCATATAAAGAAAAACCTATCCAAAA
CCAAGCAAAATCAGTAGATGTTGAGTATACCGTGCAGTTTACACCGCTTAACCCCGACGATGATTT
CCGCCCTGGATTAAAAGACACCAAATTACTGAAAACTTTAGCAATTGGCGACACCATTACCTCACA
AGAACTGTTAGCACAAGCACAATCTATCCTTAACAAAACGCACCCCGGCTATACCATTTACGAACG
CGACTCCTCTATTGTAACCCACGACAACGATATTTTCCGCACTATTCTGCCAATGGATCAAGAATT
CACCTACCATGTAAAAAACCGCGAACAGGCTTACGAAATTAACAAAAAATCTGGTTTAAACGAAG
AAATTAATAATACTGACCTGATCTCAGAAAAATATTACGTGCTGAAAAAAGGAGAAAAACCGTAT
GATCCGTTTGATCGCAGCCATCTGAAACTTTTCACCATCAAATATGTCGATGTAAACACCAACGAA
CTTTTAAAATCTGAACAATTACTTACCGCCTCCGAACGCAACTTGGATTTCCGTGATCTGTACGACC
CTCGTGATAAAGCTAAACTCTTATACAACAACCTGGATGCCTTTGGAATTATGGACTATACGTTAA
CCGGCAAAGTTGAAGACAATCACGATGACACCAACCGCATTATTACTGTTTACATGGGGAAACGG
CCTGAGGGAGAAAATGCCTCTTATCATCTTGCTTACGATAATGACCGCTATACCGAAGAAGAACGC
GAAGTCTATTCCTATCTGCGCTATACTGGAACACCTATCCCCGACAACCCTAATGACAAActcgag

FIG. 1

(SEQ ID NO:4)
MASMTGGQQM GRDPIAGPEW LLDRPSVNNS QLVVSVAGTV EGTNQDISLK FFEIDLTSRP
AHGGKTEQGL SPNSKPFATD SGAMPHKLEK ADLLKAIQEQ LIANVHSNDD YFEVIDFASD
ATITDRNGKV YFADKDGSVT LPTQPVQEFL LSGHVRVRPY KEKPIQNQAK SVDVEYTVQF
TPLNPDDDFR PGLKDTKLLK TLAIGDTITS QELLAQAQSI LNKTHPGYTI YERDSSIVTH
DNDIFRTILP MDQEFTYHVK NREQAYEINK KSGLNEEINN TDLISEKYYV LKKGEKPYDP
FDRSHLKLFT IKYVDVNTNE LLKSEQLLTA SERNLDFRDL YDPRDKAKLL YNNLDAFGIM
DYTLTGKVED NHDDTNRIIT VYMGKRPEGE NASYHLAYDN DRYTEEEREV YSYLRYTGTP
IPDNPNDKLE HHHHHH

FIG. 2

(SEQ ID NO:5)
MSDKIIHLTD DSFDTDVLKA DGAILVDFWA EWCGPCKMIA PILDEIADEY QGKLTVAKLN
IDQNPGTAPK YGIRGIPTLL LFKNGEVAAT KVGALSKGQL KEFLDANLAG SGSGHMHHHH
HHSSGLVPRG SGMKETAAAK FERQHMDSPD LGTDDDDKAM AISDPIAGPE WLLDRPSVNN
SQLVVSVAGT VEGTNQDISL KFFEIDLTSR PAHGGKTEQG LSPNSKPFAT DSGAMPHKLE
KADLLKAIQE QLIANVHSND DYFEVIDFAS DATITDRNGK VYFADKDGSV TLPTQPVQEF
LLSGHVRVRP YKEKPIQNQA KSVDVEYTVQ FTPLNPDDDF RPGLKDTKLL KTLAIGDTIT
SQELLAQAQS ILNKTHPGYT IYERDSSIVT HDNDIFRTIL PMDQEFTYHV KNREQAYEIN
KKSGLNEEIN NTDLISEKYY VLKKGEKPYD PFDRSHLKLF TIKYVDVNTN ELLKSEQLLT
ASERNLDFRD LYDPRDKAKL LYNNLDAFGI MDYTLTGKVE DNHDDTNRII TVYMGKRPEG
ENASYHLAYD NDRYTEEERE VYSYLRYTGT PIPDNPNDKL ELEHHHHHH

FIG. 3

(SEQ ID NO:6)
```
MSPILGYWKI KGLVQPTRLL LEYLEEKYEE HLYERDEGDK WRNKKFELGL EFPNLPYYID
GDVKLTQSMA IIRYIADKHN MLGGCPKERA EISMLEGAVL DIRYGVSRIA YSKDFETLKV
DFLSKLPEML KMFEDRLCHK TYLNGDHVTH PDFMLYDALD VVLYMDPMCL DAFPKLVCFK
KRIEAIPQID KYLKSSKYIA WPLQGWQATF GGGDHPPKSD GSTSGSGHHH HHHSAGLVPR
GSTAIGMKET AAAKFERQHM DSPDLGTGGG SGDDDDKSPM DIGDPIAGPE WLLDRPSVNN
SQLVVSVAGT VEGTNQDISL KFFEIDLTSR PAHGGKTEQG LSPNSKPFAT DSGAMPHKLE
KADLLKAIQE QLIANVHSND DYFEVIDFAS DATITDRNGK VYFADKDGSV TLPTQPVQEF
LLSGHVRVRP YKEKPIQNQA KSVDVEYTVQ FTPLNPDDDF RPGLKDTKLL KTLAIGDTIT
SQELLAQAQS ILNKTHPGYT IYERDSSIVT HDNDIFRTIL PMDQEFTYHV KNREQAYEIN
KKSGLNEEIN NTDLISEKYY VLKKGEKPYD PFDRSHLKLF TIKYVDVNTN ELLKSEQLLT
ASERNLDFRD LYDPRDKAKL LYNNLDAFGI MDYTLTGKVE DNHDDTNRII TVYMGKRPEG
ENASYHLAYD NDRYTEEERE VYSYLRYTGT PIPDNPNDKL EHHHHHHHH
```

FIG. 4

COMPOSITION, METHOD, AND KIT FOR PREPARING PLASMIN

CROSS-REFERENCE TO RELATED APPLICATIONS

This application is a national phase of International Application PCT/US09/046,152, filed Jun. 3, 2009, which claims priority under 35 USC §119 to U.S. Provisional Application No. 61/058,677, filed Jun. 4, 2008, each of which is herein incorporated by reference in its entirety.

FIELD OF THE INVENTION

The present invention relates to compositions and methods for preparing plasmin, in particular to compositions and methods for preparing plasmin using immobilized streptokinase.

BACKGROUND OF THE INVENTION

Blood clots consist of a fibrous network that is capable of dissolution by the proteolytic enzyme, plasmin. The enzyme is derived from the inactive proenzyme, plasminogen, a component of blood plasma, by the action of a plasminogen activator. There are two immunologically distinct mammalian plasminogen activators. Intrinsic plasminogen activator, also known as urokinase, is an enzyme produced by the kidney and can be isolated from urine. It can also be prepared from a number of tissue culture sources. Extrinsic plasminogen activator, also known as vascular plasminogen activator and as tissue plasminogen activator (t-PA), can be isolated from many tissue homogenates (notably human uterus), the vascular cell wall and from some cell cultures. In addition to these two kinds of plasminogen activator, there is also a bacterial product, streptokinase (streptokinase), prepared from *streptococci*.

With the escalating use of arterial and venous catheters in the clinics, locally delivered active plasmin offers an attractive therapeutic opportunity in thrombolytic therapy or opening clogged catheters. There are a number of reasons for this: 1) Being an active serine protease, plasmin is a direct clot dissolving agent in contrast to plasminogen activators, which require the presence of the substrate (plasminogen) in the vicinity of the clot; 2) Local catheter directed thrombolytic therapy with active plasmin can be intensified to whatever level is required to achieve completeness of clot lysis; 3) Plasmin also has the theoretical potential to be a safer thrombolytic because the lower dosage required for local delivery may decrease or even eliminate bleeding complications associated with high dose thrombolytic therapy and any potential spillage of plasmin activity from the immediate vicinity of the thrombus site will be quickly neutralized by circulating $\alpha_2$-antiplasmin.

There are several technical challenges associated with plasmin purification, especially with its therapeutic use and delivery. Plasmin is an active serine protease which is prone to autodigestion and inactivation at physiological pH. Unfortunately, plasmin degradation is most noticeable in the pH range required for manifestation of its function, clot lysis.

Current processes for commercial activation of plasma-derived plasminogen to plasmin employ soluble streptokinase in a reaction carried out in the liquid phase. The plasmin product of this activation reaction is not fully stabilized against self-proteolysis until the activation step has proceeded to the desired extent of conversion of plasminogen to plasmin. During this activation, streptokinase is cleaved by plasmin, necessitating the removal of multiple molecular species of streptokinase from the final product. Further, newly formed plasmin molecules can also begin cleaving other plasmin/plasminogen molecules, resulting in loss of valuable product, i.e., plasmin.

Thus, there is presently a need for simple and efficient methods or processes to prepare plasmin. It is additionally desirable that such a method provides plasmin solutions substantially free of the streptokinase, such that, if desired, the plasmin can be used for administering (e.g., parenterally) as a pharmaceutical.

SUMMARY OF THE INVENTION

In one aspect, the present invention provides a composition comprising a streptokinase immobilized on a matrix. The streptokinase is a streptokinase mutant characterized as capable of activating plasminogen to plasmin, yet resistant to plasmin degradation relative to its corresponding wild-type streptokinase.

In another aspect, the present invention provides an article of manufacture comprising a matrix having a streptokinase immobilized thereon, wherein the streptokinase is a streptokinase mutant characterized as capable of activating plasminogen to plasmin, yet resistant to plasmin degradation relative to its corresponding wild-type streptokinase.

In some aspects, the present invention provides a method for preparing plasmin. The method comprises:
  a) contacting a composition comprising a plasminogen with a streptokinase immobilized on a matrix thereby converting the plasminogen to a plasmin; and
  b) purifying the plasmin.

In other aspects, the present invention provides a kit for preparing plasmin. The kit comprises:
  a) a streptokinase immobilized on a matrix, wherein the streptokinase is a streptokinase mutant characterized as capable of activating plasminogen to plasmin, yet resistant to plasmin degradation relative to its corresponding wild-type streptokinase; and
  b) a plasmin-binding matrix having a molecule disposed thereon having affinity for the plasmin.

BRIEF DESCRIPTION OF THE DRAWINGS

FIG. 1 shows a nucleotide sequence (i.e., SEQ ID NO:3) comprising an open reading frame (as represented by the upper case letters) encoding a double mutant streptokinase polypeptide. The open reading frame is shown flanked by restriction enzyme sites (as represented by the lower case letters) provided for cloning.

FIG. 2 shows the amino acid sequence (SEQ ID NO:4) of the polypeptide product of a pET21 expression vector (pET System, Novagen, Madison, Wis.) comprising the open reading frame (as represented by the upper case letters) shown in SEQ ID NO:3. The lysine (K) to arginine (N) mutations in the streptokinase polypeptide are single-underlined. The isoleucine (I) amino acid residue corresponding to the N-terminus of the streptokinase sequence is double-underlined.

FIG. 3 shows the amino acid sequence (SEQ ID NO:5) of the polypeptide product of a pET32 expression vector (pET System, Novagen, Madison, Wis.) comprising the open reading frame (as represented by the upper case letters) shown in SEQ ID NO:3. The lysine (K) to arginine (N) mutations in the streptokinase polypeptide are single-underlined. The isoleucine (I) amino acid residue corresponding to the N-terminus of the streptokinase sequence is double-underlined.

FIG. 4 shows the amino acid sequence (SEQ ID NO:6) of the polypeptide product of a pET41 expression vector (pET System, Novagen, Madison, Wis.) comprising the open reading frame (as represented by the upper case letters) shown in SEQ ID NO:3. The lysine (K) to arginine (N) mutations in the streptokinase polypeptide are single-underlined. The isoleucine (I) amino acid residue corresponding to the N-terminus of the streptokinase sequence is double-underlined.

DETAILED DESCRIPTION

Figure 5:
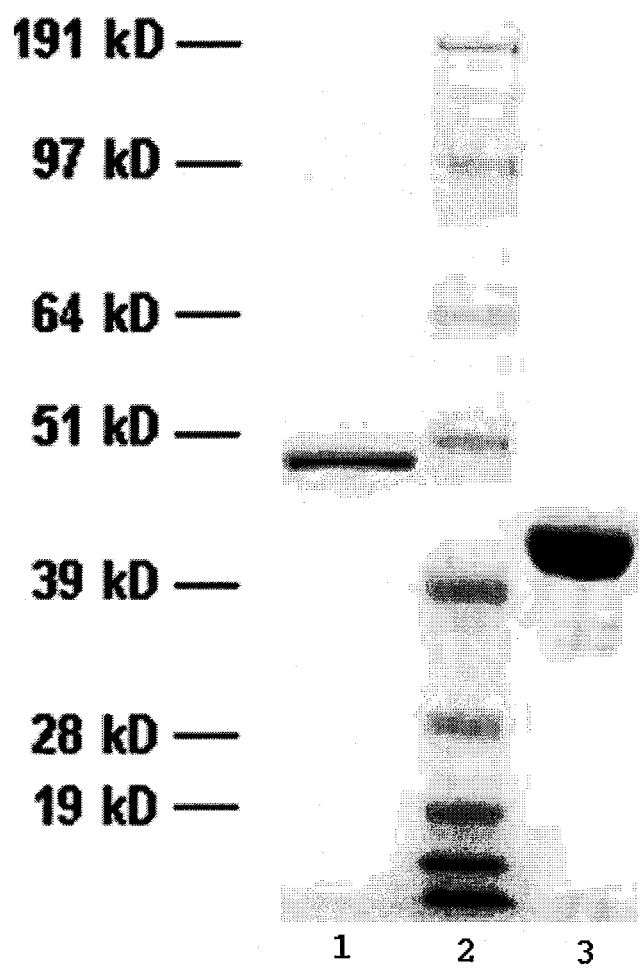
FIG. 5 shows a Coomassie Blue stained SDS-PAGE of purified recombinant streptokinase (lane 1); molecular weight markers: SeeBlue® Plus 2 molecular weight (MW) marker (Life Technologies Corp., Carlsbad, Calif.) (lane 2); and recombinant plasminogen (lane 3).

In accordance with the present invention, the plasmin purification method disclosed herein is simple, effective, reproducible, and robust. The method can produce sufficient amounts of highly pure plasmin with activity comparable with potential activity of purified plasminogen preparations. The purification can at least preserve the plasmin activity, if not enrich it. The final plasmin has minimal or no contamination with streptokinase as its presence is undesirable for therapeutic use. In one embodiment, the plasmin purification method comprises the following major steps: step a: activation of plasminogen to plasmin using immobilized streptokinase, wherein the streptokinase is a streptokinase mutant characterized as capable of activating plasminogen to plasmin, yet resistant to plasmin degradation relative to its corresponding wild-type streptokinase; and step b: capturing of active plasmin on a plasmin-capturing matrix such as, e.g., Benzamidine-SEPHAROSE. Optionally, the method further comprises elution of the bound plasmin with low pH buffer; and, further optionally, formulation of final plasmin in acidified to pH 3.7 water.

1. Streptokinase

Naturally occurring as well as recombinant streptokinase are contemplated by the present invention. Without being held to a particular theory, it is believed that streptokinase's activation mechanism involves formation of a stoichiometric complex with plasminogen.

The term "naturally-occurring" as used herein as applied to streptokinase refers to the fact that the streptokinase can be isolated from a source in nature and which has not been intentionally modified by man in the laboratory. Naturally occurring is intended to include naturally occurring "mutant" forms of streptokinase that are plasmin-resistant relative to a naturally occurring "wild-type" streptokinase.

"Recombinant" streptokinase refers to streptokinase produced by recombinant DNA techniques, i.e., produced from cells transformed by an exogenous DNA construct encoding the desired streptokinase, which can be wild-type streptokinase or a plasmin-resistant mutant.

"Synthetic" streptokinases are those prepared by chemical synthesis.

Naturally-occurring streptokinase is produced by certain Streptococci and certain bacteria which contain appropriate genetic material derived from Streptococci of Lancefield groups A, C or G. For example, streptokinase can be prepared from cultures of S. equisimilis strain H46A.

Numerous methods of purifying streptokinase have been described including, e.g., U.S. Pat. Nos. 2,701,227, 2,702,781, 2,677,642, 2,677,643, 2,691,620, 2,784,145, 3,226,304, 3,255,094, 3,419,472, 3,444,045, 3,980,772, 4,381,346, RE32271, and 5,334,384, which are incorporated herein by reference.

Streptokinase, unlike streptolysin or streptodornase, which are typical contaminating proteins which make up the impurities in naturally-occurring streptokinase preparations, does not contain the amino acids cysteine or cystine (Einarsson et al., Biochim, Biophys. Acta 568:19-29 (1979); De Renzo et al., J. Biol. Chem. 242, 533-542 (1967)). It has been suggested that this structural difference can be exploited to provide a method for the purification of streptokinase from the fermentation broth. For example, U.S. Pat. No. 5,334,384, describes a process for the separation of streptokinase from contaminating proteins in a streptokinase-containing mixture, which comprises treating the mixture with a reducing agent to reduce disulphide bridges in the contaminating proteins to free thiol groups, contacting the mixture with a reagent capable of reacting with a free thiol group and with a thiol-containing matrix, and thereafter separating the resulting chemically modified contaminating proteins from the mixture to provide streptokinase in a form substantially free of contaminating proteins.

The gene encoding for streptokinase has been isolated from its natural source (Streptococcus species) and cloned into several heterologous micro-organisms such as yeast (Hagenson et al., Enzyme. Microb. Technol. 11:650 (1989)), bacteria viz., E. coli (Malke et al., Proc. Nat'l Acad. Sci. 81:3557 (1984)), alternate species of Streptococcus (Malke et al., Mol. Gen. Genet. 196:360 (1984)), and Bacillus (Wong et al., Applied and Env. Microbiol 1:517 (1994)), all of which are incorporated herein by reference for their teachings relevant to isolation and cloning of streptokinase. Further, Caballero et al., Infection and Immunity, 67:6478-6486 (1999) is incorporated herein by reference to the extent it teaches, cloning and characterization of streptokinases secreted by porcine and equine isolates of Streptococcus equisimilis and use of matrix to immobilize a recombinant protein.

Table 1 shows the amino acid sequence of streptokinase encoded by the streptokinase gene from Streptococcus equisimilis strain H46A as disclosed by Malke et al., Gene 34:357-362 (1985) (See also GenBank Accession No. 1106184A), which are incorporated herein by reference.

TABLE 1

Amino acid sequence for streptokinase according to GENBANK
Accession No. 1106184A
Amino Acid Sequence†
(SEQ ID NO: 1)

```
  1 MKNYLSFGMF ALLFALTFGT VNSVQAIAGP EWLLDRPSVN NSQLVVSVAG TVEGTNQDIS

61 LKFFEIDLTS RPAHGGKTEQ GLSPKSKPFA TDSGAMSHKL EKADLLKAIQ EQLIANVHSN

121 DDYFEVIDFA SDATITDRNG KVYFADKDGS VTLPTQPVQE FLLSGHVRVR PYKEKPIQNQ

181 AKSVDVEYTV QFTPLNPDDD FRPGLKDTKL LKTLAIGDTI TSQELLAQAQ SILNKNHPGY

241 TIYERDSSIV THDNDIFRTI LPMDQEFTYR VKNREQAYRI NKKSGLNEEI NNTDLISEKY

301 YVLKKGEKPY DPFDRSHLKL FTIKYVDVDT NELLKSEQLL TASERNLDFR DLYDPRDKAK

361 LLYNNLDAFG IMDYTLTGKV EDNHDDTNRI ITVYMGKRPE GENASYHLAY DKDRYTEEER

421 EVYSYLRYTG TPIPDNPNDK
```

†The 26 amino acids corresponding to the signal sequence is underlined (the mature protein begins with isoleucine (I) at position 27).
Lysine (K) residues at position 85 and 412 are double-underlined (K: Lysine).

Further, streptokinase is available commercially such as, for example, streptokinase from β-hemolytic *Streptococcus* (Lancefield Group C) (Sigma-Aldrich Corp., St. Louis, Mo.) and recombinant streptokinase produced in *E. Coli* by chromatographic techniques (ABR-Affinity BioReagents Inc., Golden, Colo.). Further, genetically modified streptokinase derivatives containing "Kringle" type fibrin binding domains derived from plasminogen, and methods of obtaining the same by recombinant DNA techniques, have been described (EU 0397 366 A1).

In some embodiments, the streptokinase to be immobilized is recombinant streptokinase (e.g., recombinant wild-type or plasmin-resistant mutant) prepared by expression from recombinant DNA either in vivo or in vitro. Recombinant technology is routine and well known in the art. Amino acid affinity tags can be introduced by polymerase chain reaction. Expression can be performed in vivo using either bacteria (e.g., *E. coli*), lower eukaryotes (e.g., *Saccharomyces cerevisiae, Saccharomyces pombe, Pichia pastoris*) or higher eukaryotes (e.g., bacculo-infected insect cells, insect cells mammalian cells), or in vitro (*E. coli* lysates, wheat germ extracts, reticulocyte lysates). The streptokinase can be purified by affinity chromatography using commercially available resins.

DNA sequences encoding amino acid affinity tags and adaptor proteins can be engineered into the expression vectors such that the genes of interest can be cloned in frame either 5' or 3' of the DNA sequence encoding the affinity tag and adaptor protein. The vector can contain an origin of replication and a gene capable of conferring antibiotic resistance to a host cell. The insert of the vector can comprise a promoter sequence, a gene encoding the streptokinase of interest, optionally, a sequence encoding a polypeptide affinity tag, and a termination signal sequence. Optionally, the vector can also comprises a sequence which codes for a polypeptide adaptor molecule, preferably positioned between the protein and affinity-tag coding regions.

For in vivo expression of the proteins, cDNAs can be cloned into commercial expression vectors (e.g., as provided by Qiagen, Novagen, Clontech) and introduced into the appropriate organism for expression. For in vitro expression PCR-amplified DNA sequences can be directly used in coupled in vitro transcription/translation systems (e.g., *E. coli* S30 lysates from T7 RNA polymerase expressing, preferably protease-deficient strains, wheat germ lysates, reticulocyte lysates with and without microsomes (e.g., as provided by Promega, Pharmacia, Panvera)).

PCR reactions can be carried out under standard conditions or optimized without undue experimentation. Oligonucleotide primers can contain unique restriction sites to facilitate cloning into expression vectors. Alternatively, the TA cloning system (Clontech Laboratories, Inc., Mountain View, Calif.) can be used. Expression vectors contain the sequences for affinity tags and the protein adaptors. PCR products are ligated into the expression vectors (under inducible promoters) and introduced into the appropriate competent *E. coli* strain by calcium-dependent transformation (strains include: XL-1 blue, BL21, SG13009(lon-)). Cultures can be grown to mid-log phase, induced for expression, and cells collected by centrifugation. Cells can be resuspended containing lysozyme and the membranes broken by rapid freeze/thaw cycles, or by sonication. Cell debris can be removed by centrifugation and the appropriate affinity matrix can be added to supernatants. The streptokinase of interest is bound and non-specifically bound proteins removed by repeated washing steps. Alternatively, magnetic affinity beads and filtration devices can be used (QIAGEN, Inc., Valencia, Calif.).

*Saccharomyces cerevisiae* allows for core glycosylation and lipid modifications of proteins. The approach described above for *E. coli* can be used with slight modifications for transformation and cell lysis. Transformation of *Saccharomyces cerevisiae* can be by lithium-acetate and cell lysis can be either by lyticase digestion of the cell walls followed by freeze-thaw, sonication or glass-bead extraction. If desired, variations of post-translational modifications can be obtained by different yeast strains (i.e. *Saccharomyces pombe, Pichia pastoris*).

The advantage of the bacculovirus system or mammalian cells are the wealth of post-translational modifications that can be obtained. The bacculo-system requires cloning of viruses, obtaining high titer stocks and infection of liquid insect cell suspensions (cells are SF9, SF21). Mammalian cell-based expression requires transfection and cloning of cell lines. Soluble proteins are collected from the medium while intracellular or membrane bound proteins require cell lysis (either detergent solubilization, freeze-thaw). Proteins can then be purified analogous to the procedure described for *E. coli*.

For in vitro translation the system of choice is *E. coli* lysates obtained from protease-deficient and T7 RNA polymerase overexpressing strains. *E. coli* lysates provide efficient protein expression (30-50 μg/ml lysate). The entire process is carried out in 96-well arrays. Genes of interest are amplified by PCR using oligonucleotides that contain the gene-specific sequences containing a T7 RNA polymerase promoter and binding site and a sequence encoding the affinity tag. Alternatively, an adaptor protein can be fused to the gene of interest by PCR. Amplified DNAs can be directly transcribed and translated in the *E. coli* lysates without prior cloning for fast analysis. The proteins are then isolated by binding to an affinity matrix and processed as described above.

In one embodiment, the streptokinase is a streptokinase mutant characterized as capable of activating plasminogen to plasmin, yet resistant to plasmin degradation relative to its corresponding wild-type streptokinase. In another embodiment, the streptokinase comprises an amino acid sequence having an amino acid other than lysine at a position corresponding to position 85, 412, or both in SEQ ID NO:1. In some embodiments, the amino acid other than lysine at the position corresponding to position 85, 412, or both in SEQ ID NO:1 is asparagine or glutamine. In one embodiment, the streptokinase polypeptide comprises the amino acid sequence as shown in SEQ ID NO:2 (Table 2). In another embodiment, the streptokinase polypeptide comprises amino acid residues 27-440 as shown in SEQ ID NO:2 (Table 2).

TABLE 2

Amino acid sequence corresponding to a plasmin-resistant streptokinase in accordance with one embodiment.
Amino Acid Sequence†
(SEQ ID NO: 2)

```
  1 MKNYLSFGMF ALLFALTFGT VNSVQAIAGP EWLLDRPSVN NSQLVVSVAG TVEGTNQDIS

61 LKFFEIDLTS RPAHGGKTEQ GLSPNSKPFA TDSGAMSHKL EKADLLKAIQ EQLIANVHSN

121 DDYFEVIDFA SDATITDRNG KVYFADKDGS VTLPTQPVQE FLLSGHVRVR PYKEKPIQNQ

181 AKSVDVEYTV QFTPLNPDDD FRPGLKDTKL LKTLAIGDTI TSQELLAQAQ SILNKNHPGY

241 TIYERDSSIV THDNDIFRTI LPMDQEFTYR VKNREQAYRI NKKSGLNEEI NNTDLISEKY

301 YVLKKGEKPY DPFDRSHLKL FTIKYVDVDT NELLKSEQLL TASERNLDFR DLYDPRDKAK

361 LLYNNLDAFG IMDYTLTGKV EDNHDDTNRI ITVYMGKRPE GENASYHLAY DNDRYTEEER

421 EVYSYLRYTG TPIPDNPNDK
```

†The 26 amino acids corresponding to a signal sequence are underlined (the mature protein begins with isoleucine (I) at position 27).
K85N and K412N mutations are double-underlined (K: lysine; N: asparagine).

Alternative systems which may be used include wheat germ extracts and reticulocyte extracts. In vitro synthesis of membrane proteins and or post-translationally modified proteins will require reticulocyte lysates in combination with microsomes.

a) Plasmin-Resistant Streptokinase

Streptokinase is a labile protein susceptible to degradation in reaction with plasmin. Plasmin-degraded streptokinase fragments have been shown to exhibit lower activities as a plasminogen activator in comparison with the native streptokinase (Shi et al., Biochem. J. 304: 235-241 (1994)). The peptide bonds of the streptokinase molecule that are hydrolyzed by plasmin were previously determined (Shi et al., supra). Plasmin specifically catalyzes the hydrolysis of peptide bonds having at the amino side Lys and Arg. More specifically, the peptide bond Lys59-Ser60 of streptokinase is among the few peptide bonds which are cleaved in the early reaction with plasmin while the NH$_2$-terminal peptide, Ile1-Lys59, is essential in stabilizing the structure of streptokinase (Shi et al., supra). Therefore, a more stable streptokinase mutant can be constructed by site-directed mutagenesis or other amenable genetic cloning techniques in that the early hydrolysis of the peptide bond Lys59-Ser60 by plasmin can be prevented.

Mutant forms of streptokinase are described in, for example, U.S. Pat. Nos. 5,876,99, 5,854,049, 6,413,759, 6,309,873, and Wu et al., Applied and Environmental Microbiology, 64:824-829 (1998), which are all incorporated herein in their entirety.

In other embodiments, the streptokinase sequence, optionally, further comprises polar or charged residues at one or more positions corresponding to positions 406-410 in SEQ ID NO:1.

2. Immobilized Streptokinase

Immobilized streptokinase can be used to activate plasminogen to plasmin. This approach provides for little or no contamination of the final preparation with the streptokinase itself. Multiple ways exist to immobilize streptokinase.

Streptokinase can be adsorbed onto a suitable matrix. For example, it has been reported that streptokinase is still capable of activating plasminogen to plasmin when streptokinase is bound tightly to nitrocellulose (Kulisek et al., Analytical Biochemistry 177:78-84 (1989)). Also, adsorption of streptokinase to a suitable ion-exchange resin can render it immobilized and still capable of activating plasminogen.

Immobilized streptokinase has been described by Rimon et al., Biochem. Biophy. Acta 73:301 (1963) using a diazotized copolymer of p-aminophenylalanine and leucine. These authors utilized the immobilized streptokinase to study the mechanism of activation of plasminogen. Sugitachi et al., Thrombos. Haemostas (Stuttg.) 39:426 (1978) reported the immobilization of the plasminogen activator, urokinase, on nylon. U.S. Pat. No. 4,305,926, incorporated herein by reference, proposes immobilization of streptokinase onto a biocompatible polymer such as a nylon, Dacron, collagen, polyvinylpyrolidine, or copolymeric p-aminophenylalanine and leucine.

In one embodiment, the streptokinase is immobilized on a surface using an affinity tag as described in U.S. Pat. No. 6,406,921, which is incorporated herein by reference in its entirety. The surface can be either organic or inorganic, biological or non-biological, or any combination of these materials. In one embodiment, the surface is transparent or translucent. Numerous materials are suitable for use as a surface. For example, the surface can comprise a material selected from a group consisting of silicon, silica, quartz, glass, controlled pore glass, carbon, alumina, titanium dioxide, germanium, silicon nitride, zeolites, and gallium arsenide. Many metals such as gold, platinum, aluminum, copper, titanium, and their alloys are also options for surfaces. In addition, many ceramics and polymers can also be used. Polymers which may be used as surfaces include, but are not limited to, the following: polystyrene; poly(tetra)fluorethylene; (poly) vinylidenedifluoride; polycarbonate; polymethylmethacrylate; polyvinylethylene; polyethyleneimine; poly(etherether) ketone; polyoxymethylene (POM); polyvinylphenol; polylactides; polymethacrylimide (PMI); polyalkenesulfone (PAS); polyhydroxyethylmethacrylate; polydimethylsiloxane; polyacrylamide; polyimide; co-block-polymers; and copolymers of methacrylamide, N,N'-methylen-bis(acrylamide) and a monomer carrying oxirane groups, e.g., Eupergit™ (Röhm GmbH & Co. KG). Photoresists, polymerized Langmuir-Blodgett films, and LIGA structures may also serve as surfaces in the present invention.

The term "affinity tag" is used herein to refer to a functional moiety capable of immobilizing a protein onto the exposed functionality of a surface. In some cases, the affinity tag may be a simple chemical functional group. Other possibilities include amino acids, polypeptides, proteins, lipid bilayers, or a hydrogel. The affinity tag may be either covalently or non-covalently attached to the protein (via chemical conjugation or as a fusion protein, for instance). Likewise, the affinity tag may bind to the surface layer either covalently or noncovalently.

An "adaptor molecule", for purposes of this invention, is any entity that links an affinity tag to a protein. The adaptor molecule need not necessarily be a discrete molecule that is noncovalently attached to both the affinity tag and the protein. The adaptor molecule can be covalently attached to the affinity tag or the protein or both (via chemical conjugation or as a fusion protein, for instance). In some cases, an affinity tag may also be an internal part of the protein, such as an amino acid. Examples of adaptor molecules include polypeptides, proteins, membrane anchors, and biotin.

The term "fusion protein" refers to a protein composed of two or more polypeptides that, although typically unjoined in their native state, are joined by their respective amino and carboxyl termini through a peptide linkage to form a single continuous polypeptide. It is understood that the two or more polypeptide components can either be directly joined or indirectly joined through a peptide linker/spacer.

A layer of organic molecules can be coated on the surface. One face of the layer can be composed of chemical functionalities on the termini of the organic molecules that are chemisorbed or physisorbed onto the surface material (headgroups). The other face of the layer can be exposed and may bear any number of chemical functionalities (end groups). In some embodiments, the molecules of the layer are highly ordered and tightly packed, largely due to hydrophobic and van der Waals interactions between the molecules.

The affinity tag can enhance immobilization of the streptokinase on the surface. The affinity tag can confer enhanced binding or reaction of the streptokinase with a functional group. The affinity tag/functional group pair can allow for immobilization of the streptokinase on the surface in a manner which does not require harsh reaction conditions that are adverse to streptokinase stability or function. The affinity tag also can offer immobilization that is specific to a designated site or location on the streptokinase. For this to occur, attachment of the affinity tag to the streptokinase protein should be site-specific. This site specific immobilization can help ensure that the reactive site of the protein remains accessible to ligands in solution. Another advantage of immobilization through affinity tags is that it allows for a common immobilization strategy to be used with multiple, different proteins.

In some embodiments, the affinity tag comprises at least one amino acid. The affinity tag may be a polypeptide comprising at least one reactive amino acid. Alternatively, the affinity tag may be a lone, organic molecule layer-reactive amino acid such as, for example, cysteine, lysine, histidine, arginine, tyrosine, and glutamine. A polypeptide or amino acid affinity tag is preferably expressed as a fusion protein with the protein. Amino acid tags provide either a single amino acid or a series of amino acids that can interact with the functional group of the layer molecules. Amino acid affinity tags can be readily introduced into recombinant proteins to facilitate oriented immobilization by covalent binding to the bioreactive Y-functional group of the monolayer.

The affinity tag may comprise a poly(amino acid) tag. A poly(amino acid) tag is a polypeptide that comprises from about 2 to about 100 residues of a single amino acid, optionally interrupted by residues of other amino acids. For instance, the affinity tag may comprise a poly-cysteine, poly-lysine, poly-arginine, or poly-histidine. Amino acid tags are preferably composed of two to twenty residues of a single amino acid, such as, for example, histidines, lysines, arginines, cysteines, glutamines, tyrosines, or any combination of these.

In one embodiment, an amino acid tag of one to twenty amino acids comprises at least one to ten cysteines for thioether linkage; or one to ten lysines for amide linkage; or one to ten arginines for coupling to vicinal dicarbonyl groups. One of ordinary skill in the art can readily pair suitable affinity tags with a given Y-functionality.

The position of the amino acid tag can be at the amino-, or carboxy-terminus of the streptokinase protein or anywhere in-between. Where compatible with protein function, affinity tags introduced for protein purification are preferentially located at the C-terminus of the recombinant protein to ensure that only full-length proteins are isolated during protein purification.

Affinity tags may also contain one or more unnatural amino acids. Unnatural amino acids can be introduced using suppressor tRNAs that recognize stop codons (i.e. amber) (Noren et al., Science, 1989, 244:182-188; Ellman et al., Methods Enzym., 1991, 202:301-336; Cload et al., Chem. Biol., 1996, 3:1033-1038). The tRNAs are chemically amino-acylated to contain chemically altered ("unnatural") amino acids for use with specific coupling chemistries (i.e. ketone modifications, photoreactive groups).

In some embodiments, the affinity tag comprises a whole protein, such as, but not limited to, glutathione S-transferase, an antibody, avidin, or streptavidin.

Other protein conjugation and immobilization techniques known in the art may be adapted for the purpose of immobilizing the streptokinase on surface. For example, the affinity tag may be an organic bioconjugate which is chemically coupled to streptokinase. Biotin or antigens may be chemically cross linked to streptokinase. Alternatively, a chemical cross linker may be used that attaches a simple functional moiety such as a thiol or an amine to the surface of streptokinase.

In other embodiments, the affinity tag is a component of an affinity tag layer immobilized on the layer of organic molecules of the surface. For instance, a hydrogel composed of a material such as dextran can serve as a suitable affinity tag layer. Use of such hydrogels to immobilize protein is described in U.S. Pat. No. 5,242,828. Poly-lysine is another option for a material useful in forming an affinity tag layer (for an example see U.S. Pat. No. 5,629,213). The affinity tag layer could also constitute a phospholipid bilayer or a phospholipid monolayer as described in PCT Publication WO 96/38726.

In still further embodiments, an adaptor molecule can link the affinity tag to the immobilized streptokinase. The additional spacing of the protein from the surface that is afforded by the use of an adaptor molecule can be advantageous as proteins may be prone to surface inactivation. One of ordinary skill in the art will be able to choose an adaptor molecule which is appropriate for a given affinity tag. For instance, if the affinity tag is streptavidin, then the adaptor could be a biotin molecule that is chemically conjugated to the streptokinase which is to be immobilized. Alternatively, if the affinity tag is a phospholipid biolayer or monolayer then a membrane anchor could be chosen as a suitable adaptor molecule.

In one embodiment, the adaptor molecule is a polypeptide, such as protein G or protein A. In another embodiment, the affinity tag, adaptor molecule, and protein together compose a fusion protein. Such a fusion protein may be readily expressed using standard recombinant DNA technology. Adaptor proteins are especially useful to increase the solubility of the protein of interest and to increase the distance between the surface and the protein of interest. Examples of possible adaptor proteins include glutathione-S-transferase (GST), maltose-binding protein, chitin-binding protein, thioredoxin, green-fluorescent protein (GFP). GFP can also be used for quantification of surface binding.

In another embodiment, recombinant streptokinase can be immobilized using immobilized metal ion adsorption chromatography (IMAC). This chromatography method, which is an especially sensitive separation technique and also applicable to most types of proteins, is a technique commonly used in purification schemes together with another chromatographic step, such ion exchange chromatography (IEX) and/ or hydrophobic interaction chromatography (HIC).

IMAC utilizes matrices that comprises a group capable of forming a chelate with a transition metal ion, which chelate in turn is used as the ligand in chromatography to adsorb a compound from a liquid. The binding strength in IMAC is affected predominately by the species of metal ion, the pH of the buffers, and the nature of the ligand used. Because the metal ions are strongly bound to the matrix, the adsorbed protein can, optionally, be eluted either by lowering the pH or by competitive elution.

In general, IMAC is useful for separation of proteins or other molecules that present an affinity for the transition metal ion of the matrix. For example, proteins will bind to the matrix upon the presence of accessible histidine, cysteine and tryptophan residues, which all exhibit an affinity for the chelated metal.

In one embodiment, the streptokinase can be tagged with one or more histidine residues in order to increase their affinity to metal chelated ligands.

Simple chelators have been suggested as ligands for IMAC, such as iminodiacetic acid (IDA). IDA, coupled to agarose supports and subsequent charged with various metals, such as $Cu^{2+}$, $Zn^{2+}$, and $Ni^{2+}$, has been used for capture of proteins and peptides and is also available as commercial resins. More specifically, U.S. Pat. No. 4,551,271 (Hochuli, assigned to Hoffmann-La Roche Inc.), which is incorporated herein by reference, discloses a metal chelate resin which comprises IDA ligands. The resin can according to the specification be prepared in a known manner by treating agarose with epichlorohydrin or epibromohydrin, reacting the resulting epoxide with iminoacetic acid disodium salt and converting the product into the copper or zinc salt by washing with a copper (II) or zinc solution.

EP 87109892.7 (F. Hoffmann-La Roche AG) and its equivalent U.S. Pat. No. 4,877,830 (Döbeli et al., assigned to Hoffmann-La Roche Inc.), which are both incorporated herein by reference for their teaching of immobilizing a protein using metal chelate resins.

WO 01/81365 (Sigma-Aldrich Co.), Which is incorporated herein by reference for its teaching of metal chelating compositions that according to the specification is capable of forming relatively stable chelates With metal ions and exhibits an improved selectivity for polyhistidine tagged proteins. The disclosed compositions are coupled to an insoluble carrier, such as crosslinked beaded agarose, e.g., SEPHAROSE™ (GE Healthcare) according to given examples.

Lizano et al., J. Microbiol. Methods, 23:261-280 is incorporated herein by reference for its teaching of use of matrix to immobilize a recombinant protein.

The compositions of the present invention also can be supplied in kit form. Accordingly, in other aspects, the present invention provides a kit for preparing plasmin. The kit comprises a streptokinase immobilized on a matrix, wherein the streptokinase is a streptokinase mutant characterized as capable of activating plasminogen to plasmin, yet resistant to plasmin degradation relative to its corresponding wild-type streptokinase. The streptokinase is as described above.

In one embodiment, the kit further comprises a plasminbinding matrix having a molecule disposed thereon having affinity for the plasmin.

Kits can comprise the various components in separate containers. For example, the containers can separately comprise the streptokinase, matrix, etc. such that when combined with other components of the kit together provide for compositions and methods for preparing plasmin. Packaged compositions and kits of this invention also can include instructions for storage, preparation, and the like.

The present invention will be illustrated in more detail by way of Examples, but it is to be noted that the invention is not limited to the Examples.

EXAMPLES

Example 1

Preparation of Recombinant Tagged Streptokinase

The DNA molecule shown in FIG. 1 (i.e., SEQ ID NO:3), which comprises a nucleic acid sequence encoding a doublemutant streptokinase protein was synthesized (Blue Heron Biotech, Bothell, Wash.) and cloned (to facilitate cloning, a 5' BamHI and a 3' XhoI site was included) into the commercially available vectors pET21b, pET32b, and pET41b (EMD Millipore (formerly Novagen®), Billerica, Mass.) to produce several recombinant polypeptides (FIGS. 2-4, respectively) comprising an amino acid sequence corresponding to a plasmin-resistant streptokinase appended at the C- and/or N-terminus with various tags including polyhistidine, thioredoxin, and GST. These tags facilitated affinity purification of three recombinant streptokinase molecules using the corresponding resin and buffer kits according to the manufacturer's protocols and as described in the pET System Manual, 11$^{th}$ edition, which is incorporated herein for its teaching of target gene cloning, expression, and affinity purification of target proteins.

All three recombinant streptokinase DNA constructs were transformed into *E. coli* BL21(DE3) Gold competent cells (Stratagene, La Jolla, Calif.) and grown using Luria-Bertani (LB) media. Typically, about 0.5 mL of an overnight seed culture was grown at 37° C. and used to inoculate about 200 mL of fresh LB media. For the pET21b and pET32b constructs, the LB media was supplemented with 50 μg/mL of ampicillin, while the pET 41b construct was grown in the presence of 30 μg/mL kanamycin. Each culture was grown to an $OD_{595\ nm}$ of approximately 0.7, and then induced by the addition of isopropyl β-D-1-thiogalactopyranoside (IPTG) to 1.0 mM. Following four hours of growth at 37° C., the cells from the cultures were harvested via centrifugation and frozen at −20° C. until required for use.

The initial recombinant streptokinase purification steps for all three constructs were similar, and involved cell lysis and clarification. Thawed cell pellets were resuspended in 20 mL of bacterial protein extraction reagent (BPER) (Pierce, Rockford, Ill.) and then incubated at room temperature for 10 minutes. The lysed cultures were clarified by centrifugation for 20 minutes at 15K (Sorvall SS34 rotor in a RC5C centrifuge), and filtered through a 0.22 □m filter.

A 5 mL cobalt charged HiTrap Chelating HP (GE Healthcare Bio-Sciences Corp, Piscataway, N.J.) column was used to purify recombinant streptokinase from the pET21b- and pET32b-derived cultures (poly-histidine tagged variants). Clarified cell lysate was applied to the cobalt charged HiTrap Chelating column at 5 mLs/min following equilibration with 20 mM sodium phosphate, 500 mM NaCl, and 10 mM imidazole, pH 7.4. Post-loading, the column was washed extensively with the above buffer. Protein elution was initiated by the application of 20 mM sodium phosphate, 500 mM NaCl, and 500 mM imidazole, pH 7.4 elution buffer. Absorbance measurements taken at 280 nm were used to monitor the progression of the purification run using a GE Healthcare AKTA Explorer chromatography instrument. Fractions containing the target recombinant streptokinase protein during elution as determined by SDS-PAGE electrophoresis were pooled, and buffer exchanged for additional purification using anion exchange chromatography.

A 5 mL HiTrap Q-Sepharose column (GE Healthcare Bio-Sciences Corp, Piscataway, N.J.) equilibrated with 25 mM Tris-HCl, and 1 mM EDTA, pH 8.0 was used to further purify the eluate fractions obtained from the immobilized cobalt column. Following overnight dialysis against the Q-Sepharose equilibration buffer, the pooled fractions were applied to the Q-Sepharose column at 5 mLs/min. Following loading the column was washed extensively with equilibration buffer. Protein was eluted from the Q-Sepharose column by the application of NaCl elution buffer (25 mM Tris-HCl, 1.0 M NaCl, and 1 mM EDTA, pH 8.0). A 0-100% elution buffer gradient developed over 20 minutes was used to eluate the target protein.

The pET41 GST-fusion protein was purified from clarified cell lysate using a 5 mL GSTrap FF column (GE Healthcare Bio-Sciences Corp, Piscataway, N.J.). Clarified cell lysate was applied to the column equilibrated with phosphate buffered saline (PBS). Loading was followed by extensive washing with PBS, and protein elution was achieved with 50 mM Tris-HCl, and 10 mM glutathione, pH 8.0. SDS-PAGE, anti-streptokinase Western blotting, and activation assays confirmed the identify of all three purified proteins.

FIG. 5 shows an example of a Coomasie Blue stained SDS-PAGE gel of a purified recombinant streptokinase as well as purified recombinant plasminogen.

Example 2

Preparation of Immobilized Polyhistidine-Tagged Plasmin-Resistant Mutant Streptokinase Histidine-tagged (plasmin-resistant) streptokinase (100 μg) in 10 mM Tris-HCl (pH 8.0) and 100 mM NaCl is added to 100 μl of metal-chelating IMAC affinity matrix. After incubation at 22° C. for 5 min, the slurry is applied to a Spin-X microcentrifuge spin column (Costar, Cambridge, Mass.) fitted with a 0.45-μm cellulose acetate filter. The matrix is pelleted by centrifugation at 2,000×g for 3 min and is subsequently washed several times with 20 mM Tris-HCl, pH 7.4. The matrix is removed from the Spin-X unit, placed in a microcentrifuge tube, and resuspended in 200 ml of 50 mM Tris-HCl buffer, pH 7.4.

Example 3

Preparation of Plasminogen

Plasma-derived plasminogen can be prepared as described in e.g., U.S. Pat. Nos. 6,964,764 and 6,969,515, which are incorporated herein by reference in their entirety. For example, plasminogen is purified from Cohn Fraction II+III paste by affinity chromatography on Lys-Sepharose as described by Deutsch et al., Science, 170:1095 (1970). Thus, 200 g of the paste is resuspended in 2 liter of 0.15M sodium citrate buffer, pH 7.8. The suspension is incubated overnight at 37° C., centrifuged at 14,000 rpm, filtered through fiberglass and mixed with 500 ml of Lys-Sepharose 4B (Pharmacia). Binding of plasminogen is at room temperature for 2 hours. The Lys-Sepharose is then transferred onto a 2-liter glass filter, and washed several times with 0.15M sodium citrate containing 0.3M NaCl until the absorbance at 280 nm dropped below 0.05. Bound plasminogen is eluted with three 200-ml portions of 0.2M ε-aminocaproic acid. Eluted plasminogen is precipitated with 0.4 g solid ammonium sulfate/ml of plasminogen solution. The precipitate of crude (80-85% pure) plasminogen can be stored at 4° C.

Example 4

Activation of Plasminogen to Plasmin Using Immobilized Polyhistidine-Tagged Plasmin-Resistant Mutant Streptokinase An equimolar amount of plasminogen is added to the immobilized streptokinase in 50 mM Tris-HCl buffer, pH 7.4. Samples are incubated at 22° C. and placed on a rotating platform to keep the matrix in suspension. Upon completion of activation, the plasmin solution is filtered from streptokinase-SEPHAROSE on a glass filter and immediately applied on benzamidine-SEPHAROSE.

To monitor the progress of plasminogen activation, at different intervals, a sample is selected and the reaction is terminated by the addition of 0.1 volumes of 10× stop buffer (1.0 M $NaHCO_3$, 1.0 M ε-aminocaproic acid [pH 9.4]). The sample is transferred to a Spin-X microcentrifuge tube and pelleted by centrifugation at 2,000×g for 3 min. Immobilized reactants are eluted by addition of 25 ml of 100 mM EDTA, followed by centrifugation at 5,000×g for 10 min. Samples are prepared for SDS-PAGE analysis by addition of 25 ml of 2⅔ SDS buffer containing β-mercaptoethanol, boiled for 5 min, and applied to an SDS-10% polyacrylamide gel.

Example 5

Activation of Recombinant Plasminogen by Tagged Plasmin-Resistant Streptokinase in Solution Purified recombinant streptokinase produced with the pET21b expression construct was dialysed against 25 mM Tris-HCl, pH 7.0, 100 mM εACA, 1 mM EDTA, and 25% glycerol (v:v). Affinity purified recombinant plasminogen in the same buffer was mixed with recombinant streptokinase at mole ratios of 100:1, 10:1, and 1:1. The amount of streptokinase in each of these three reactions was held constant, while the amount of recombinant plasminogen was varied to produce the various recombinant plasminogen to streptokinase mole ratios. The two components were mixed and incubated at room temperature for up to 18 hours. At time 0, 1, 2, 3, 4 and 18 hours into the activation reaction an aliquot of the mixture was removed, and prepared for SDS-PAGE electrophoresis. The SDS-PAGE samples were treated according to the NuPAGE Novex BisTris sample preparation protocol (Invitrogen, Carlsbad, Calif.) using reducing conditions. 4-12% BisTris gels in MOPS buffer were used for the SDS-PAGE experiments.

Figure 6:
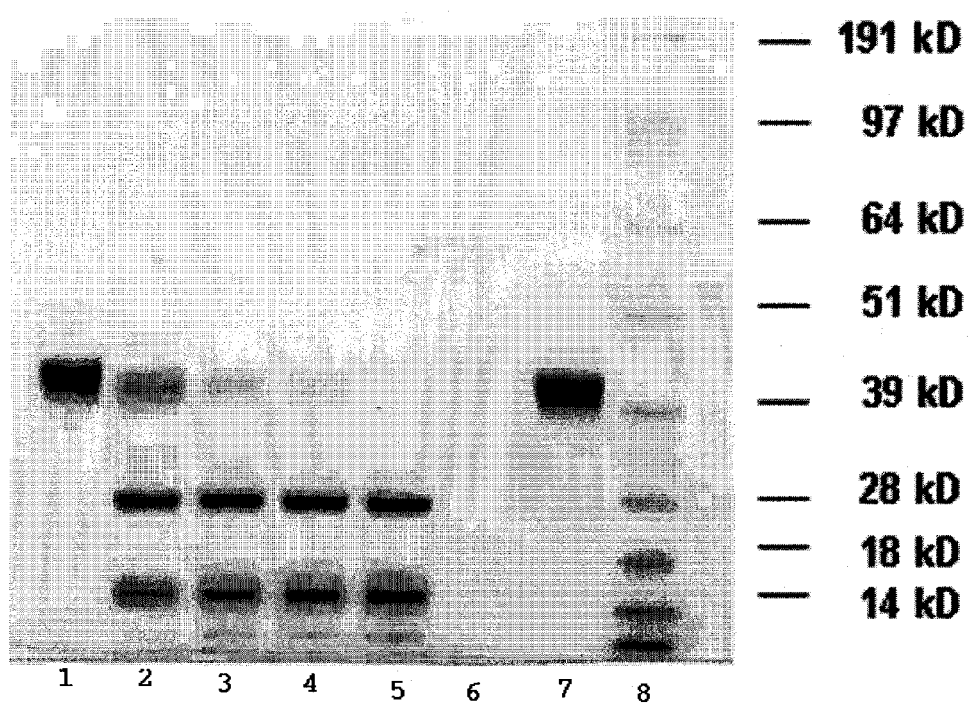
FIG. 6 is an SDS-PAGE showing a time course for conversion of recombinant plasminogen to recombinant plasmin as catalyzed by recombinant streptokinase. Time=0 hour (lane 1); 2 hours (lane 2); 4 hours (lane 3); 6 hours (lane 4); and 18 hours (lane 5). Lanes 6, 7, and 8 correspond to recombinant streptokinase control, recombinant plasminogen control, and MW marker (SeeBlue® Plus 2), respectively.

As shown in FIG. 6 for the 100:1 mole ratio of recombinant plasminogen:recombinant streptokinase, activation of recombinant plasminogen to recombinant plasmin by recombinant streptokinase was evident on SDS-PAGE. The time course of activation revealed that recombinant plasminogen is converted to recPlamsin by early on in the reaction, evident by the formation of two bands under reducing PAGE conditions. The band observed migrating near the 28 kD marker is the serine protease domain of recPlasminogen, while the smaller band migrating just above the 14 kD marker is the kringle domain. Concomitant with the appearance of these two bands was the disappearance of the recombinant plasminogen starting material at 39 kD. At t=18 hours into the reaction, nearly all of the recombinant plasminogen had been converted to recombinant plasmin.

For the 10:1 mole ratio reaction, SDS-PAGE could barely be used to track the experiment, while the amount of total protein present in the 1:1 mole ratio experiment was too little for SDS-PAGE monitoring (data not shown).

From the SDS-PAGE gel data shown in FIG. 6, it is evident that purified recombinant streptokinase (pET 21b construct) has the ability to convert recombinant plasminogen to rec-Plasmin.

To monitor the fate of recombinant streptokinase in the activation reactions, Western blotting experiments were required to monitor reaction progress. SDS-PAGE gels of all three time course reactions were run as noted above, and then transferred to PVDF membranes according the the Novex X Cell II blot module protocol (Invitrogen, Carlsbad, Calif.). Blocking of the PVDF membrane was conducted with a 1% BSA solution in phosphate buffered saline (Sigma-P3688, St. Louis, Mo.), while Tris buffered saline (Sigma-T9039, St. Louis, Mo.) was used for all washing and antibody dilution solutions. Following electrophoretic transfer and blocking of the PVDF membrane, the blot was probed with polyclonal rabbit anti-streptokinase antibodies (AbD Serotec (0100-0173), Raleigh, N.C.) using a 1:4000 dilution of the stock 1° antibody. Goat anti-rabbit IgG antibodies (Sigma-A3937, St. Louis, Mo.) labeled with alkaline phosphatase were used at a 1:5000 fold dilution in conjunction with Sigma Fast BCIP/NBT substrate (Sigma-B5655, St. Louis, Mo.) to visualize the streptokinase fragments.

Figure 7:
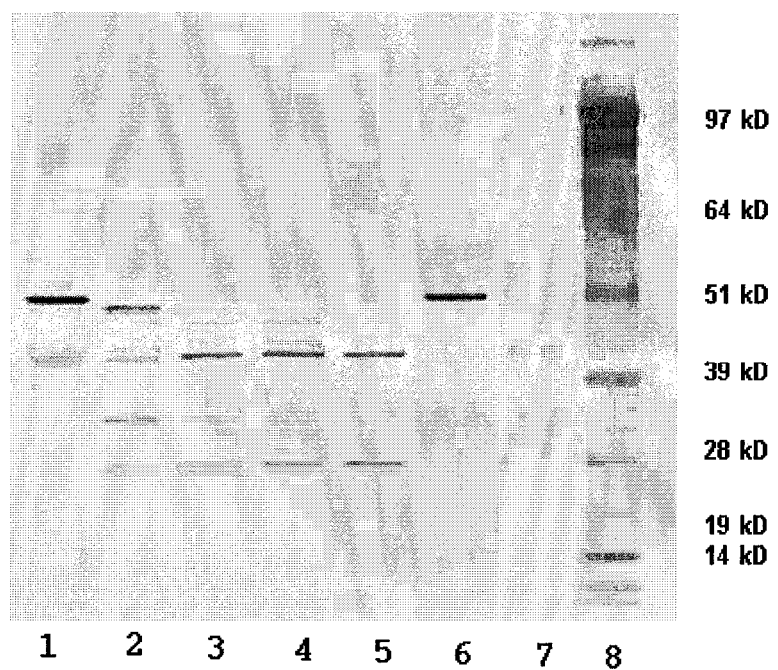
FIG. 7 is a Western blot of the time course experiment shown in FIG. 6 using polyclonal anti-streptokinase antibodies. Time=0 hour (lane 1); 2 hours (lane 2); 4 hours (lane 3); 6 hours (lane 4); and 18 hours (lane 5). Lanes 6, 7, and 8 correspond to recombinant streptokinase control, recombinant plasminogen control, and MW marker (SeeBlue® Plus 2), respectively.

As shown in FIG. 7, under reaction conditions where recombinant plasminogen is incubated with recombinant streptokinase (100:1 mole ratio), the streptokinase molecules were proteolysed to a number of species in a time dependent manner. The initial proteolytic cut removed a small portion of the polypeptide backbone, evident by the formation of a band below the 51 kD marker on the Western blot. With increasing reaction time, this fragment further degraded and passed through a number of transient species until it formed a stable species that migrated above the 39 and 51 kD MW markers. The initial appearance of a fuzzy band at that same location on the blot was due to cross reactivity of the 1° antibody to full length recombinant plasminogen. The recombinant plasminogen control (lane 7) and the t=0 reaction sample (lane 1), both demonstrated this cross reactivity. At longer reaction times as recombinant plasminogen was being consumed, the fuzzy band diminished, and a new sharp band representing the core streptokinase fragment appeared. Cross reactivity was also apparent with the serine protease (SP) domain of recombinant plasmin (data not shown).

For the 1:1 mole ratio experiment, the rate of activation was diminished significantly (data not shown). At t=4 hours into the reaction, the first signs of streptokinase proteolysis were apparent. Under these reaction conditions, a very stable streptokinase fragment was generated, even at t=18 hours into the reaction. This was likely the result of all of the streptokinase being tied up in a complex with recombinant plasmin, with very little free recombinant plasmin available to degrade the recombinant streptokinase molecules.

The results show that early in the activation reaction, recombinant streptokinase breaks down to a number of transient species, but at later times forms a stable polypeptide with an apparent MW above 39 kD.

Example 6

Capturing Plasmin on Benzamidine-SEPHAROSE

Affinity chromatography is a useful technique in protein purification. Because the protein of interest is an active serine protease (i.e., plasmin) with trypsin-like specificity, benzamidine-SEPHAROSE is chosen as an affinity sorbent which would allow the capture of only the active plasmin and would leave behind the various contaminants and plasminogen degradation products. Plasmin capturing, elution, and formulation is described in e.g., U.S. Pat. No. 6,355,243, which is incorporated herein by reference in its entirety.

Completely activated plasminogen solution in 50% glycerol is applied to the 50 ml benzamidine-SEPHAROSE column equilibrated with 0.05 M Tris, pH 8.0, 0.5 M NaCl with a flow rate of 3 ml/min. The column is run at 3 ml/min at 4° C.

Example 7

Elution of the Bound Plasmin with Low pH Buffer

In order to preserve plasmin from inactivation at neutral pH, acidic elution conditions are chosen. The plasmin bound to benzamidine-SEPHAROSE is eluted with 0.2 M glycine buffer, pH 3.0 containing 0.5 M NaCl. The bound peak is typically divided into three pools, small two front portions of the peak, B1 and B2, and the bulk of the eluted material, B3.

Example 8

Formulation of Eluted Material in Acidified Water

Eluted plasmin is dialyzed with water which has been acidified, for example to pH of about 3.3 to about 3.7 with glacial acetic acid. Initially, this solvent condition is chosen simply to maintain active plasmin while preparing it for the future formulation procedures such as lyophilization, freezing, changing the solvent conditions and so on. All of these latter procedures are easier to perform with non-buffered, low-ionic strength solution. But we find that plasmin is extremely stable in acidified water and can be effectively used in this form for in vitro and in vivo studies.

What is claimed is:

1. A method for preparing plasmin, the method comprising:
   (a) contacting a composition comprising a plasminogen with a streptokinase immobilized on a matrix thereby converting the plasminogen to a plasmin, wherein the streptokinase is a streptokinase mutant characterized as capable of activating plasminogen to plasmin, yet resistant to plasmin degradation relative to its corresponding wild-type streptokinase; and wherein the streptokinase comprises an amino acid sequence having an amino acid residue other than lysine at a position corresponding to position 85, 412, or both positions, as shown in SEQ ID NO:1; and
   (b) purifying the plasmin by a method comprising contacting the composition with a plasmin-binding matrix so that the plasmin is retained by the plasmin-binding matrix, the plasmin-binding matrix having a molecule disposed thereon having affinity for the plasmin.

2. The method of claim 1, wherein the streptokinase comprises the amino acid sequence shown as amino acid residues 27 through 440 of SEQ ID NO:2.

3. The method of claim 1, wherein the streptokinase, optionally, further comprises polar or charged amino acid residues comprising lysine, arginine, histidine, aspartic acid, glutamic acid, serine, threonine, asparagine, glutamine, tryosine or cysteine at one or more positions corresponding to positions 406-410 in SEQ ID NO:1.

4. The method of claim 1, wherein the amino acid residue is glutamine or asparagine.

5. The method of claim 2, wherein the streptokinase, optionally, further comprises polar or charged amino acid residues comprising lysine, arginine, histidine, aspartic acid, glutamic acid, serine, threonine, asparagine, glutamine, tryosine or cysteine at one or more positions corresponding to positions 406-410 in SEQ ID NO:1.

6. The method of claim 1, wherein the streptokinase is recombinant.

7. The method of claim 1, wherein the streptokinase comprises an affinity tag.

8. The method of claim 7, wherein the affinity tag comprises polyhistidine, thioredoxin, or glutathione-S-transferase (GST).

9. The method of claim 7, wherein the affinity tag comprises polyhistidine.

10. The method of claim 1, wherein the streptokinase is immobilized on a matrix comprising immobilized metal ion adsorption chromatography.

11. The method of claim 1, wherein the plasma-binding matrix is benzamidine-coupled to crosslinked beaded agarose.

12. The method of claim 1, wherein the plasminogen is plasma-derived.

13. The method of claim 1, wherein the plasminogen is recombinant.

14. A method for preparing plasmin, the method comprising:
(a) contacting a composition comprising a plasminogen with a streptokinase immobilized on a matrix thereby converting the plasminogen to a plasmin,
wherein the streptokinase is a streptokinase mutant characterized as capable of activating plasminogen to plasmin, yet resistant to plasmin degradation relative to its corresponding wild-type streptokinase;
wherein the streptokinase comprises an amino acid sequence having an amino acid residue other than lysine at a position corresponding to position 85, 412, or both positions, as shown in SEQ ID NO:1; and
wherein the streptokinase comprises a polyhistidine affinity tag; and
(b) purifying the plasmin by a method comprising contacting the composition with a plasmin-binding matrix so that the plasmin is retained by the plasmin-binding matrix;
wherein the plasma-binding matrix is benzamidine-coupled to crosslinked beaded agarose.

15. The method of claim 14, wherein the streptokinase comprises the amino acid sequence shown as amino acid residues 27 through 440 of SEQ ID NO:2.

16. The method of claim 14, wherein the streptokinase, optionally, further comprises polar or charged amino acid residues comprising lysine, arginine, histidine, aspartic acid, glutamic acid, serine, threonine, asparagine, glutamine, tryosine or cysteine at one or more positions corresponding to positions 406-410 in SEQ ID NO:1.

17. The method of claim 14, wherein the amino acid residue is glutamine or asparagine.

18. The method of claim 15, wherein the streptokinase, optionally, further comprises polar or charged amino acid residues comprising lysine, arginine, histidine, aspartic acid, glutamic acid, serine, threonine, asparagine, glutamine, tryosine or cysteine at one or more positions corresponding to positions 406-410 in SEQ ID NO:1.

19. The method of claim 14, wherein the plasminogen is plasma-derived.

20. The method of claim 14, wherein the plasminogen is recombinant.

* * * * *

```
                        SEQUENCE LISTING

<160> NUMBER OF SEQ ID NOS: 6

<210> SEQ ID NO 1
<211> LENGTH: 440
<212> TYPE: PRT
<213> ORGANISM: Streptococcus equisimilis

<400> SEQUENCE: 1

Met Lys Asn Tyr Leu Ser Phe Gly Met Phe Ala Leu Leu Phe Ala Leu
1               5                   10                  15

Thr Phe Gly Thr Val Asn Ser Val Gln Ala Ile Ala Gly Pro Glu Trp
            20                  25                  30

Leu Leu Asp Arg Pro Ser Val Asn Asn Ser Gln Leu Val Val Ser Val
        35                  40                  45

Ala Gly Thr Val Glu Gly Thr Asn Gln Asp Ile Ser Leu Lys Phe Phe
    50                  55                  60

Glu Ile Asp Leu Thr Ser Arg Pro Ala His Gly Gly Lys Thr Glu Gln
65                  70                  75                  80

Gly Leu Ser Pro Lys Ser Lys Pro Phe Ala Thr Asp Ser Gly Ala Met
                85                  90                  95

Ser His Lys Leu Glu Lys Ala Asp Leu Leu Lys Ala Ile Gln Glu Gln
            100                 105                 110

Leu Ile Ala Asn Val His Ser Asn Asp Asp Tyr Phe Glu Val Ile Asp
        115                 120                 125

Phe Ala Ser Asp Ala Thr Ile Thr Asp Arg Asn Gly Lys Val Tyr Phe
    130                 135                 140

Ala Asp Lys Asp Gly Ser Val Thr Leu Pro Thr Gln Pro Val Gln Glu
145                 150                 155                 160

Phe Leu Leu Ser Gly His Val Arg Val Arg Pro Tyr Lys Glu Lys Pro
                165                 170                 175

Ile Gln Asn Gln Ala Lys Ser Val Asp Val Glu Tyr Thr Val Gln Phe
            180                 185                 190

Thr Pro Leu Asn Pro Asp Asp Asp Phe Arg Pro Gly Leu Lys Asp Thr
        195                 200                 205

Lys Leu Leu Lys Thr Leu Ala Ile Gly Asp Thr Ile Thr Ser Gln Glu
    210                 215                 220

Leu Leu Ala Gln Ala Gln Ser Ile Leu Asn Lys Asn His Pro Gly Tyr
225                 230                 235                 240

Thr Ile Tyr Glu Arg Asp Ser Ser Ile Val Thr His Asp Asn Asp Ile
                245                 250                 255

Phe Arg Thr Ile Leu Pro Met Asp Gln Glu Phe Thr Tyr Arg Val Lys
            260                 265                 270

Asn Arg Glu Gln Ala Tyr Arg Ile Asn Lys Lys Ser Gly Leu Asn Glu
        275                 280                 285

Glu Ile Asn Asn Thr Asp Leu Ile Ser Glu Lys Tyr Tyr Val Leu Lys
    290                 295                 300

Lys Gly Glu Lys Pro Tyr Asp Pro Phe Asp Arg Ser His Leu Lys Leu
```

```
                305                 310                 315                 320
Phe Thr Ile Lys Tyr Val Asp Val Asp Thr Asn Glu Leu Leu Lys Ser
                325                 330                 335

Glu Gln Leu Leu Thr Ala Ser Glu Arg Asn Leu Asp Phe Arg Asp Leu
                340                 345                 350

Tyr Asp Pro Arg Asp Lys Ala Lys Leu Leu Tyr Asn Asn Leu Asp Ala
                355                 360                 365

Phe Gly Ile Met Asp Tyr Thr Leu Thr Gly Lys Val Glu Asp Asn His
            370                 375                 380

Asp Asp Thr Asn Arg Ile Ile Thr Val Tyr Met Gly Lys Arg Pro Glu
385                 390                 395                 400

Gly Glu Asn Ala Ser Tyr His Leu Ala Tyr Asp Lys Asp Arg Tyr Thr
                405                 410                 415

Glu Glu Glu Arg Glu Val Tyr Ser Tyr Leu Arg Tyr Thr Gly Thr Pro
                420                 425                 430

Ile Pro Asp Asn Pro Asn Asp Lys
                435                 440

<210> SEQ ID NO 2
<211> LENGTH: 440
<212> TYPE: PRT
<213> ORGANISM: Artificial Sequence
<220> FEATURE:
<223> OTHER INFORMATION: recombinant

<400> SEQUENCE: 2

Met Lys Asn Tyr Leu Ser Phe Gly Met Phe Ala Leu Leu Phe Ala Leu
1               5                   10                  15

Thr Phe Gly Thr Val Asn Ser Val Gln Ala Ile Ala Gly Pro Glu Trp
                20                  25                  30

Leu Leu Asp Arg Pro Ser Val Asn Asn Ser Gln Leu Val Val Ser Val
                35                  40                  45

Ala Gly Thr Val Glu Gly Thr Asn Gln Asp Ile Ser Leu Lys Phe Phe
            50                  55                  60

Glu Ile Asp Leu Thr Ser Arg Pro Ala His Gly Gly Lys Thr Glu Gln
65                  70                  75                  80

Gly Leu Ser Pro Asn Ser Lys Pro Phe Ala Thr Asp Ser Gly Ala Met
                85                  90                  95

Ser His Lys Leu Glu Lys Ala Asp Leu Leu Lys Ala Ile Gln Glu Gln
                100                 105                 110

Leu Ile Ala Asn Val His Ser Asn Asp Tyr Phe Glu Val Ile Asp
            115                 120                 125

Phe Ala Ser Asp Ala Thr Ile Thr Asp Arg Asn Gly Lys Val Tyr Phe
            130                 135                 140

Ala Asp Lys Asp Gly Ser Val Thr Leu Pro Thr Gln Pro Val Gln Glu
145                 150                 155                 160

Phe Leu Leu Ser Gly His Val Arg Val Arg Pro Tyr Lys Glu Lys Pro
                165                 170                 175

Ile Gln Asn Gln Ala Lys Ser Val Asp Val Glu Tyr Thr Val Gln Phe
                180                 185                 190

Thr Pro Leu Asn Pro Asp Asp Phe Arg Pro Gly Leu Lys Asp Thr
            195                 200                 205

Lys Leu Leu Lys Thr Leu Ala Ile Gly Asp Thr Ile Thr Ser Gln Glu
            210                 215                 220

Leu Leu Ala Gln Ala Gln Ser Ile Leu Asn Lys Asn His Pro Gly Tyr
225                 230                 235                 240
```

```
Thr Ile Tyr Glu Arg Asp Ser Ser Ile Val Thr His Asp Asn Asp Ile
            245                 250                 255

Phe Arg Thr Ile Leu Pro Met Asp Gln Glu Phe Thr Tyr Arg Val Lys
        260                 265                 270

Asn Arg Glu Gln Ala Tyr Arg Ile Asn Lys Lys Ser Gly Leu Asn Glu
    275                 280                 285

Glu Ile Asn Asn Thr Asp Leu Ile Ser Glu Lys Tyr Tyr Val Leu Lys
290                 295                 300

Lys Gly Glu Lys Pro Tyr Asp Pro Phe Asp Arg Ser His Leu Lys Leu
305                 310                 315                 320

Phe Thr Ile Lys Tyr Val Asp Val Asp Thr Asn Glu Leu Leu Lys Ser
                325                 330                 335

Glu Gln Leu Leu Thr Ala Ser Glu Arg Asn Leu Asp Phe Arg Asp Leu
            340                 345                 350

Tyr Asp Pro Arg Asp Lys Ala Lys Leu Leu Tyr Asn Asn Leu Asp Ala
        355                 360                 365

Phe Gly Ile Met Asp Tyr Thr Leu Thr Gly Lys Val Glu Asp Asn His
    370                 375                 380

Asp Asp Thr Asn Arg Ile Ile Thr Val Tyr Met Gly Lys Arg Pro Glu
385                 390                 395                 400

Gly Glu Asn Ala Ser Tyr His Leu Ala Tyr Asn Asp Arg Tyr Thr
                405                 410                 415

Glu Glu Glu Arg Glu Val Tyr Ser Tyr Leu Arg Tyr Thr Gly Thr Pro
            420                 425                 430

Ile Pro Asp Asn Pro Asn Asp Lys
        435                 440

<210> SEQ ID NO 3
<211> LENGTH: 1255
<212> TYPE: DNA
<213> ORGANISM: Artificial Sequence
<220> FEATURE:
<223> OTHER INFORMATION: recombinant

<400> SEQUENCE: 3
ggatcccatc gctggtcccg aatggctctt agaccgtcca tctgtgaata actcccaact     60
tgtagtatcc gttgcaggca ccgtcgaagg aaccaaccaa gacatctcct taaaattttt    120
tgaaatcgat ttaacctctc gtcctgccca tggcggaaaa accgaacaag gcctctcacc    180
aaactctaaa cctttgcca ccgattcagg agctatgcca cacaaactcg aaaaagccga    240
cctcttaaaa gctatccaag aacaacttat cgctaatgta cattcaaatg atgattattt    300
tgaagtaatt gattttgcgt ctgatgccac aattaccgat cgcaatggca agtctatttt    360
tgctgataaa gacggtagcg ttaccttgcc cactcagcca gtacaggaat tcttattatc    420
cggccacgtg cgcgtacgtc catataaaga aaaacctatc caaaaccaag caaaatcagt    480
agatgttgag tataccgtgc agtttacacc gcttaaccc gacgatgatt tccgccctgg    540
attaaaagac accaaattac tgaaaacttt agcaattggc gacaccatta cctcacaaga    600
actgttagca caagcacaat ctatccttaa caaaacgcac cccggctata ccatttacga    660
acgcgactcc tctattgtaa cccacgacaa cgatattttc cgcactattc tgccaatgga    720
tcaagaattc acctaccatg taaaaaaccg cgaacaggct tacgaaatta acaaaaaatc    780
tggtttaaac gaagaaatta ataatactga cctgatctca gaaaaatatt acgtgctgaa    840
aaaaggagaa aaaccgtatg atccgtttga tcgcagccat ctgaaacttt tcaccatcaa    900
```

```
atatgtcgat gtaaacacca acgaactttt aaaatctgaa caattactta ccgcctccga   960
acgcaacttg gatttccgtg atctgtacga ccctcgtgat aaagctaaac tcttatacaa  1020
caacctggat gcctttggaa ttatggacta tacgttaacc ggcaaagttg aagacaatca  1080
cgatgacacc aaccgcatta ttactgttta catggggaaa cggcctgagg gagaaaatgc  1140
ctcttatcat cttgcttacg ataatgaccg ctataccgaa gaagaacgcg aagtctattc  1200
ctatctgcgc tatactggaa cacctatccc cgacaaccct aatgacaaac tcgag       1255
```

```
<210> SEQ ID NO 4
<211> LENGTH: 436
<212> TYPE: PRT
<213> ORGANISM: Artificial Sequence
<220> FEATURE:
<223> OTHER INFORMATION: recombinant

<400> SEQUENCE: 4

Met Ala Ser Met Thr Gly Gly Gln Gln Met Gly Arg Asp Pro Ile Ala
1               5                   10                  15

Gly Pro Glu Trp Leu Leu Asp Arg Pro Ser Val Asn Asn Ser Gln Leu
            20                  25                  30

Val Val Ser Val Ala Gly Thr Val Glu Gly Thr Asn Gln Asp Ile Ser
        35                  40                  45

Leu Lys Phe Phe Glu Ile Asp Leu Thr Ser Arg Pro Ala His Gly Gly
    50                  55                  60

Lys Thr Glu Gln Gly Leu Ser Pro Asn Ser Lys Pro Phe Ala Thr Asp
65                  70                  75                  80

Ser Gly Ala Met Pro His Lys Leu Glu Lys Ala Asp Leu Leu Lys Ala
                85                  90                  95

Ile Gln Glu Gln Leu Ile Ala Asn Val His Ser Asn Asp Tyr Phe
            100                 105                 110

Glu Val Ile Asp Phe Ala Ser Asp Ala Thr Ile Thr Asp Arg Asn Gly
        115                 120                 125

Lys Val Tyr Phe Ala Asp Lys Asp Gly Ser Val Thr Leu Pro Thr Gln
    130                 135                 140

Pro Val Gln Glu Phe Leu Leu Ser Gly His Val Arg Val Arg Pro Tyr
145                 150                 155                 160

Lys Glu Lys Pro Ile Gln Asn Gln Ala Lys Ser Val Asp Val Glu Tyr
                165                 170                 175

Thr Val Gln Phe Thr Pro Leu Asn Pro Asp Asp Phe Arg Pro Gly
            180                 185                 190

Leu Lys Asp Thr Lys Leu Leu Lys Thr Leu Ala Ile Gly Asp Thr Ile
    195                 200                 205

Thr Ser Gln Glu Leu Leu Ala Gln Ala Gln Ser Ile Leu Asn Lys Thr
210                 215                 220

His Pro Gly Tyr Thr Ile Tyr Glu Arg Asp Ser Ser Ile Val Thr His
225                 230                 235                 240

Asp Asn Asp Ile Phe Arg Thr Ile Leu Pro Met Asp Gln Glu Phe Thr
                245                 250                 255

Tyr His Val Lys Asn Arg Glu Gln Ala Tyr Glu Ile Asn Lys Lys Ser
            260                 265                 270

Gly Leu Asn Glu Glu Ile Asn Asn Thr Asp Leu Ile Ser Glu Lys Tyr
        275                 280                 285

Tyr Val Leu Lys Lys Gly Glu Lys Pro Tyr Asp Pro Phe Asp Arg Ser
    290                 295                 300

His Leu Lys Leu Phe Thr Ile Lys Tyr Val Asp Val Asn Thr Asn Glu
```

```
            305                 310                 315                 320
Leu Leu Lys Ser Glu Gln Leu Leu Thr Ala Ser Glu Arg Asn Leu Asp
                325                 330                 335

Phe Arg Asp Leu Tyr Asp Pro Arg Asp Lys Ala Lys Leu Leu Tyr Asn
                340                 345                 350

Asn Leu Asp Ala Phe Gly Ile Met Asp Tyr Thr Leu Thr Gly Lys Val
                355                 360                 365

Glu Asp Asn His Asp Asp Thr Asn Arg Ile Ile Thr Val Tyr Met Gly
            370                 375                 380

Lys Arg Pro Glu Gly Glu Asn Ala Ser Tyr His Leu Ala Tyr Asp Asn
385                 390                 395                 400

Asp Arg Tyr Thr Glu Glu Arg Glu Val Tyr Ser Tyr Leu Arg Tyr
                405                 410                 415

Thr Gly Thr Pro Ile Pro Asp Asn Pro Asn Asp Lys Leu Glu His His
                420                 425                 430

His His His His
            435

<210> SEQ ID NO 5
<211> LENGTH: 589
<212> TYPE: PRT
<213> ORGANISM: Artificial Sequence
<220> FEATURE:
<223> OTHER INFORMATION: recombinant

<400> SEQUENCE: 5

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
                35                  40                  45

Glu Tyr Gln Gly Lys Leu Thr Val Ala Lys Leu Asn Ile Asp Gln Asn
            50                  55                  60

Pro Gly Thr Ala Pro Lys Tyr Gly Ile Arg Gly Ile Pro Thr Leu Leu
65              70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
                100                 105                 110

Ser Gly His Met His His His His His Ser Ser Gly Leu Val Pro
                115                 120                 125

Arg Gly Ser Gly Met Lys Glu Thr Ala Ala Ala Lys Phe Glu Arg Gln
            130                 135                 140

His Met Asp Ser Pro Asp Leu Gly Thr Asp Asp Asp Lys Ala Met
145                 150                 155                 160

Ala Ile Ser Asp Pro Ile Ala Gly Pro Glu Trp Leu Leu Asp Arg Pro
                165                 170                 175

Ser Val Asn Asn Ser Gln Leu Val Val Ser Val Ala Gly Thr Val Glu
                180                 185                 190

Gly Thr Asn Gln Asp Ile Ser Leu Lys Phe Phe Glu Ile Asp Leu Thr
            195                 200                 205

Ser Arg Pro Ala His Gly Gly Lys Thr Glu Gln Gly Leu Ser Pro Asn
        210                 215                 220

Ser Lys Pro Phe Ala Thr Asp Ser Gly Ala Met Pro His Lys Leu Glu
225                 230                 235                 240
```

```
Lys Ala Asp Leu Leu Lys Ala Ile Gln Glu Gln Leu Ile Ala Asn Val
                245                 250                 255

His Ser Asn Asp Asp Tyr Phe Glu Val Ile Asp Phe Ala Ser Asp Ala
                260                 265                 270

Thr Ile Thr Asp Arg Asn Gly Lys Val Tyr Phe Ala Asp Lys Asp Gly
            275                 280                 285

Ser Val Thr Leu Pro Thr Gln Pro Val Gln Glu Phe Leu Leu Ser Gly
        290                 295                 300

His Val Arg Val Arg Pro Tyr Lys Glu Lys Pro Ile Gln Asn Gln Ala
305                 310                 315                 320

Lys Ser Val Asp Val Glu Tyr Thr Val Gln Phe Thr Pro Leu Asn Pro
                325                 330                 335

Asp Asp Asp Phe Arg Pro Gly Leu Lys Asp Thr Lys Leu Leu Lys Thr
                340                 345                 350

Leu Ala Ile Gly Asp Thr Ile Thr Ser Gln Glu Leu Leu Ala Gln Ala
            355                 360                 365

Gln Ser Ile Leu Asn Lys Thr His Pro Gly Tyr Thr Ile Tyr Glu Arg
        370                 375                 380

Asp Ser Ser Ile Val Thr His Asp Asn Asp Ile Phe Arg Thr Ile Leu
385                 390                 395                 400

Pro Met Asp Gln Glu Phe Thr Tyr His Val Lys Asn Arg Glu Gln Ala
                405                 410                 415

Tyr Glu Ile Asn Lys Lys Ser Gly Leu Asn Glu Glu Ile Asn Asn Thr
            420                 425                 430

Asp Leu Ile Ser Glu Lys Tyr Tyr Val Leu Lys Lys Gly Glu Lys Pro
        435                 440                 445

Tyr Asp Pro Phe Asp Arg Ser His Leu Lys Leu Phe Thr Ile Lys Tyr
    450                 455                 460

Val Asp Val Asn Thr Asn Glu Leu Leu Lys Ser Glu Gln Leu Leu Thr
465                 470                 475                 480

Ala Ser Glu Arg Asn Leu Asp Phe Arg Asp Leu Tyr Asp Pro Arg Asp
                485                 490                 495

Lys Ala Lys Leu Leu Tyr Asn Asn Leu Asp Ala Phe Gly Ile Met Asp
            500                 505                 510

Tyr Thr Leu Thr Gly Lys Val Glu Asp Asn His Asp Asp Thr Asn Arg
        515                 520                 525

Ile Ile Thr Val Tyr Met Gly Lys Arg Pro Glu Gly Glu Asn Ala Ser
    530                 535                 540

Tyr His Leu Ala Tyr Asp Asn Asp Arg Tyr Thr Glu Glu Glu Arg Glu
545                 550                 555                 560

Val Tyr Ser Tyr Leu Arg Tyr Thr Gly Thr Pro Ile Pro Asp Asn Pro
                565                 570                 575

Asn Asp Lys Leu Glu Leu Glu His His His His His His
            580                 585

<210> SEQ ID NO 6
<211> LENGTH: 709
<212> TYPE: PRT
<213> ORGANISM: Artificial Sequence
<220> FEATURE:
<223> OTHER INFORMATION: recombinant

<400> SEQUENCE: 6

Met Ser Pro Ile Leu Gly Tyr Trp Lys Ile Lys Gly Leu Val Gln Pro
1               5                   10                  15
```

```
Thr Arg Leu Leu Leu Glu Tyr Leu Glu Glu Lys Tyr Glu Glu His Leu
        20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
 50                  55                  60

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Gly Ser Thr Ser
210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Ser Gly
                260                 265                 270

Asp Asp Asp Asp Lys Ser Pro Met Asp Ile Gly Asp Pro Ile Ala Gly
        275                 280                 285

Pro Glu Trp Leu Leu Asp Arg Pro Ser Val Asn Asn Ser Gln Leu Val
 290                 295                 300

Val Ser Val Ala Gly Thr Val Glu Gly Thr Asn Gln Asp Ile Ser Leu
305                 310                 315                 320

Lys Phe Phe Glu Ile Asp Leu Thr Ser Arg Pro Ala His Gly Gly Lys
                325                 330                 335

Thr Glu Gln Gly Leu Ser Pro Asn Ser Lys Pro Phe Ala Thr Asp Ser
                340                 345                 350

Gly Ala Met Pro His Lys Leu Glu Lys Ala Asp Leu Leu Lys Ala Ile
        355                 360                 365

Gln Glu Gln Leu Ile Ala Asn Val His Ser Asn Asp Asp Tyr Phe Glu
370                 375                 380

Val Ile Asp Phe Ala Ser Asp Ala Thr Ile Thr Asp Arg Asn Gly Lys
385                 390                 395                 400

Val Tyr Phe Ala Asp Lys Asp Gly Ser Val Thr Leu Pro Thr Gln Pro
                405                 410                 415

Val Gln Glu Phe Leu Leu Ser Gly His Val Arg Val Arg Pro Tyr Lys
        420                 425                 430

Glu Lys Pro Ile Gln Asn Gln Ala Lys Ser Val Asp Val Glu Tyr Thr
        435                 440                 445
```

-continued

```
Val Gln Phe Thr Pro Leu Asn Pro Asp Asp Phe Arg Pro Gly Leu
    450                 455                 460
Lys Asp Thr Lys Leu Leu Lys Thr Leu Ala Ile Gly Asp Thr Ile Thr
465             470                 475                 480
Ser Gln Glu Leu Leu Ala Gln Ala Gln Ser Ile Leu Asn Lys Thr His
            485                 490                 495
Pro Gly Tyr Thr Ile Tyr Glu Arg Asp Ser Ser Ile Val Thr His Asp
            500                 505                 510
Asn Asp Ile Phe Arg Thr Ile Leu Pro Met Asp Gln Glu Phe Thr Tyr
        515                 520             525
His Val Lys Asn Arg Glu Gln Ala Tyr Glu Ile Asn Lys Lys Ser Gly
    530             535                 540
Leu Asn Glu Glu Ile Asn Asn Thr Asp Leu Ile Ser Glu Lys Tyr Tyr
545             550                 555                 560
Val Leu Lys Lys Gly Glu Lys Pro Tyr Asp Pro Phe Asp Arg Ser His
                565             570                 575
Leu Lys Leu Phe Thr Ile Lys Tyr Val Asp Val Asn Thr Asn Glu Leu
            580             585             590
Leu Lys Ser Glu Gln Leu Leu Thr Ala Ser Glu Arg Asn Leu Asp Phe
        595             600             605
Arg Asp Leu Tyr Asp Pro Arg Asp Lys Ala Lys Leu Leu Tyr Asn Asn
    610             615             620
Leu Asp Ala Phe Gly Ile Met Asp Tyr Thr Leu Thr Gly Lys Val Glu
625             630             635             640
Asp Asn His Asp Asp Thr Asn Arg Ile Ile Thr Val Tyr Met Gly Lys
            645                 650             655
Arg Pro Glu Gly Glu Asn Ala Ser Tyr His Leu Ala Tyr Asp Asn Asp
            660             665             670
Arg Tyr Thr Glu Glu Glu Arg Glu Val Tyr Ser Tyr Leu Arg Tyr Thr
        675             680             685
Gly Thr Pro Ile Pro Asp Asn Pro Asn Asp Lys Leu Glu His His His
    690             695             700
His His His His His
705
```